(12) United States Patent
Cheng et al.

(10) Patent No.: US 9,498,499 B2
(45) Date of Patent: Nov. 22, 2016

(54) IMAGING-AIDED GENE THERAPY USING MESENCHYMAL STEM CELLS AS TARGET-DELIVERY VEHICLE

(71) Applicant: The Board of Trustees of the Leland Stanford Junior University, Palo Alto, CA (US)

(72) Inventors: Zhen Cheng, Mountain View, CA (US); Kai Chen, Sunnyvale, CA (US); Xiaoyuan Chen, Potomac, MD (US)

( * ) Notice: Subject to any disclaimer, the term of this patent is extended or adjusted under 35 U.S.C. 154(b) by 0 days.

(21) Appl. No.: 14/395,651

(22) PCT Filed: Apr. 19, 2013

(86) PCT No.: PCT/US2013/037315
§ 371 (c)(1),
(2) Date: Oct. 20, 2014

(87) PCT Pub. No.: WO2013/158962
PCT Pub. Date: Oct. 24, 2013

(65) Prior Publication Data
US 2015/0086515 A1    Mar. 26, 2015

Related U.S. Application Data

(60) Provisional application No. 61/635,422, filed on Apr. 19, 2012.

(51) Int. Cl.
| | | |
|---|---|---|
| A61K 35/28 | (2015.01) | |
| C12N 5/0775 | (2010.01) | |
| A61K 35/12 | (2015.01) | |

(52) U.S. Cl.
CPC ............. *A61K 35/28* (2013.01); *C12N 5/0663* (2013.01); *A61K 2035/124* (2013.01); *C12N 2502/99* (2013.01)

(58) Field of Classification Search
None
See application file for complete search history.

(56) References Cited

U.S. PATENT DOCUMENTS

2005/0074426 A1    4/2005  Corti et al.
2011/0263512 A1   10/2011  Bordignon et al.

OTHER PUBLICATIONS

Wang, H. et al., "Integrin-targeted imaging and therapy with RGD4C-TNF fusion protein"; Molecular Cancer Therapeutics; May 2008, vol. 7, No. 5, pp. 1044-1053.
Hu, Yu-Lan et al., "Mesenchymal stem cells: a promising targeted-delivery vehicle in cancer gene therapy"; Journal of Controlled Release, May 19, 2010, vol. 147, No. 2, pp. 154-162.
Kai, T. et al., "RGD-based strategies for selective delivery of therapeutics and imaging agents to the tumour vasculature"; Drug Resistance Updates 8, 2005, pp. 381-402.
Zischek C. et al. Targeting tumor stroma using engineered mesenchymal stem cells reduces the growth of pancreatic carcinoma. Ann Surg. Nov. 2009;250(5):747-53.

*Primary Examiner* — Addison D Ault
(74) *Attorney, Agent, or Firm* — Thomas|Horstemeyer, LLP

(57) ABSTRACT

Compositions and methods of use thereof encompass engineered mesenchymal stem cells as a vehicle to deliver secreted tissue necrosis factor-RGD4C fusion polypeptides for tumor treatment, thereby reducing side effects of TNF. A reporter gene can be included in vector constructs to monitor the localization and viability of engineered MSCs after administration into a recipient animal. The genetically modified mesenchymal stem cell can comprise an expression cassette comprising a nucleic acid sequence operably linked to a gene expression promoter and encoding the heterologous fusion polypeptide comprising a tissue necrotic factor region and an integrin-binding region. Another aspect of the disclosure encompasses embodiments of a method of modulating the proliferation of a targeted population of tumor cells by delivering a population of the genetically modified mesenchymal stem cells to tumor cells, allowing the mesenchymal stem cells to express the heterologous polypeptide, thereby reducing the proliferative capacity of the tumor cells.

4 Claims, 15 Drawing Sheets

SEQ ID No.: 1
acgcgtgtagtcttatgcaatactcttgtagtcttgcaacatggtaacgatgagttagcaac
atgccttacaaggagagaaaaagcaccgtgcatgccgattggtggaagtaaggtggtacgat
cgtgccttattaggaaggcaacagacgggtctgacatggattggacgaaccactgaattgcc
gcattgcagagatattgtatttaagtgcctagctcgatacaataaacgggtctctctggtta
gaccagatctgagcctgggagctctctggctaactagggaacccactgcttaagcctcaata
aagcttgccttgagtgcttcaagtagtgtgtgcccgtctgttgtgtgactctggtaactaga
gatccctcagaccctttagtcagtgtggaaaatctctagcagtggcgcccgaacagggacc
tgaaagcgaaagggaaaccagagctctctcgacgcaggactcggcttgctgaagcgcgcacg
gcaagaggcgaggggcggcgactggtgagtacgccaaaaattttgactagcggaggctagaa
ggagagagatgggtgcgagagcgtcagtattaagcggggggagaattagatcgcgatgggaaa
aaattcggttaaggccaggggggaaagaaaaaatataaattaaaacatatagtatgggcaagc
agggagctagaacgattcgcagttaatcctggcctgttagaaacatcagaaggctgtagaca
aatactgggacagctacaaccatcccttcagacaggatcagaagaacttagatcattatata
atacagtagcaaccctctattgtgtgcatcaaaggatagagataaaagacaccaaggaagct
ttagacaagatagaggaagagcaaaacaaaagtaagaccaccgcacagcaagcggccactga
tcttcagacctggaggaggagatatgagggacaattggagaagtgaattatataaatataaa
gtagtaaaaattgaaccattaggagtagcacccaccaaggcaaagagaagagtggtgcagag
agaaaaaagagcagtgggaataggagctttgttccttgggttcttgggagcagcaggaagca
ctatgggcgcagcctcaatgacgctgacggtacaggccagacaattattgtctggtatagtg
cagcagcagaacaatttgctgagggctattgaggcgcaacagcatctgttgcaactcacagt
ctggggcatcaagcagctccaggcaagaatcctggctgtggaaagatacctaaaggatcaac
agctcctggggatttggggttgctctggaaaactcatttgcaccactgctgtgccttggaat
gctagttggagtaataaatctctggaacagattggaatcacacgacctggatggagtgggac
agagaaattaacaattacacaagcttaatacactccttaattgaagaatcgcaaaaccagca
agaaaagaatgaacaagaattattggaattagataaatgggcaagtttgtggaattggttta
acataacaaattggctgtggtatataaaattattcataatgatagtaggaggcttggtaggt
ttaagaatagttttgctgtactttctatagtgaatagagttaggcagggatattcaccatt
atcgtttcagacccacctcccaaccccgaggggacccgacaggcccgaaggaatagaagaag
aaggtggagagagagacagagacagatccattcgattagtgaacggatctcgacggttaact
tttaaaagaaaaggggggattgggggggtacagtgcaggggaaagaatagtagacataatagc
aacagacatacaaactaaagaattacaaaaacaaattacaaaaattcaaaattttatcgata
ctagttgaaagaccccacctgtaggtttggcaagttagcttaagtaacgccattttgcaagg
catggaaaatacataactgagaatagagaagttcagatcaaggttaggaacagagagacagc
agaatatgggccaaacaggatatctgtggtaagcagttcctgccccggctcagggccaagaa
cagatggtccccagatgcggtcccgccctcagcagtttctagcgaaccatcagatgtttcca
gggtgccccaaggacctgaaatgaccctgtgccttatttgaactaaccaatcagtttgcttc
ttgcttctgtttgtgtgcttctgctccctgagctcaataaaagagcccacaacccctcactt
ggtgggccagtcctctgatagactgtgtccctggataccgtattctagagctagcatgag
cactgaaagcatgatccgggacgtggagctggccgaggaggcgctccccaagaagacagggg
ggccccagggctccaggcggtgcttgttcctcagcctcttctccttcctgatcgtggcaggc
gccaccacgctcttctgcctgctgcactttggagtgatcggcccccagagggaagagttccc
cagggacctctctctaatcagccctctggcccaggcagtcagatcatcttctcgaaccccga
gtgacaagcctgtagcccatgttgtagcaaaccctcaagctgaggggcagctccagtggctg

*Fig. 8*

```
aaccgccgggccaatgccctcctggccaatggcgtggagctgagagataaccagctggtggt
gccatcagagggcctgtacctcatctactcccaggtcctcttcaagggccaaggctgcccct
ccacccatgtgctcctcacccacaccatcagccgcatcgccgtctcctaccagaccaaggtc
aacctcctctctgccatcaagagcccctgccagagggagaccccagaggggctgaggccaa
gccctggtatgagcccatctatctgggagggtcttccagctggagaagggtgaccgactca
gcgctgagatcaatcggcccgactatctcgactttgccgagtctgggcaggtctactttggg
atcattgccctgtgcgattgccgtggtgattgcttttgctgagcggccgcaaggatctgcga
tcgctccggtgcccgtcagtgggcagagcgcacatcgcccacagtccccgagaagttggggg
gagggggtcggcaattgaacgggtgcctagagaaggtggcgcggggtaaactgggaaagtgat
gtcgtgtactggctccgccttttcccgagggtgggggagaaccgtatataagtgcagtagt
cgccgtgaacgttcttttttcgcaacgggtttgccgccagaacacagctgaagcttcgagggg
ctcgcatctctccttcacgcgcccgccgccctacctgaggccgccatccacgccggttgagt
cgcgttctgccgcctcccgcctgtggtgcctcctgaactgcgtccgccgtctaggtaagttt
aaagctcaggtcgagaccgggcctttgtccggcgctcccttggagcctacctagactcagcc
ggctctccacgctttgcctgaccctgcttgctcaactctacgtctttgtttcgttttctgtt
ctgcgccgttacagatccaagctgtgaccggcgcctacgctagacgccaccttaattaaatg
cgcttcaaggtgcgcatggagggctccgtgaacggccacgagttcgagatcgagggcgaggg
cgagggccgcccctacgagggcacccagaccgccaagctgaaggtgaccaagggcggccccc
tgcccttcgcctgggacatcctgtcccctcagttccagtacggctccaaggcctacgtgaag
caccccgccgacatccccgactacttgaagctgtccttccccgagggcttcaagtgggagcg
cgtgatgaacttcgaggacggcggcgtggtgaccgtgacccaggactcctccctgcaggacg
gcgagttcatctacaaggtgaagctgcgcggcaccaacttccctccgacggcccgtaatg
cagaagaagaccatgggctgggaggcctccaccgagcggatgtaccccgaggacggcgccct
gaagggcgagatcaagatgaggctgaagctgaaggacggcggccactacgacgccgaggtca
agaccacctacatggccaagaagcccgtgcagctgcccggcgcctacaagaccgacatcaag
ctggacatcacctcccacaacgaggactacaccatcgtggaacagtacgagcgcgccgaggg
ccgccactccaccggcgccaccgcgggcccgggatccgccaccatgcccacgctactgcggg
tttatatagacggtccccacgggatggggaaaaccaccaccaccacgcaactgctggtggcc
ctgggttcgcgcgacgatatcgtctacgtacccgagccgatgacttactggcgggtgctggg
ggcttccgagacaatcgcgaacatctacaccacacaacaccgcctcgaccagggtgagatat
cggccggggacgcggcggtggtaatgacaagcgcccagataacaatgccttatgccgtgacc
gacgccgttctggctcctcatatcggggggggaggctgggagctcacatgccccgcccccggc
cctcaccatcttcctcgaccgccatccatcgccttcatgctgtgctacccggccgcgcggt
accttatgggcagcatgaccccccaggccgtgctggcgttcgtggccctcatcccgccgacc
ttgcccggcaccaacatcgtgcttggggcccttccggaggacagacacatcgaccgcctggc
caaacgccagcgccccggcgagcggctggacctggctatgctggctgcgattcgccgcgttt
acgggctacttgccaatacggtgcggtatctgcagtgcggcgggtcgtggcgggaggactgg
ggacagctttcggggacggccgtgccgcccagggtgccgagccccagagcaacgcgggccc
acgacccccatatcggggacacgttatttaccctgtttcgggccccgagttgatggccccca
acggcgacctgtataacgtgtttgcctggccttggacgtcttggccaaacgcctccgttcc
atgcacgtctttatcctggattacgaccaatcgcccgccggctgccgggacgccctgctgca
acttacctccgggatggtccagacccacgtcaccaccccggctccataccgacgatatgcg
acctggcgcgcacgtttgcccgggagatggggggaggctaactgactcgaggtcgacaatcaa
cctctggattacaaaatttgtgaaagattgactggtattcttaactatgttgctccttttac
```

Fig. 8 (Continued)

```
gctatgtggatacgctgctttaatgcctttgtatcatgctattgcttcccgtatggctttcat
tttctcctccttgtataaatcctggttgctgtctctttatgaggagttgtggcccgttgtcag
gcaacgtggcgtggtgtgcactgtgtttgctgacgcaaccccactggttggggcattgccac
cacctgtcagctcctttccgggactttcgctttccccctccctattgccacggcggaactcat
cgccgcctgccttgccgctgctggacaggggctcggctgtgggcactgacaattccgtggt
gttgtcggggaaatcatcgtcctttccttggctgctcgcctgtgttgccacctggattctgcg
cgggacgtccttctgctacgtcccttcggccctcaatccagcggaccttccttcccgcggcct
gctgccggctctgcggcctcttccgcgtcttcgccttcgccctcagacgagtcggatctccct
ttgggccgcctccccgcctggtacctttaagaccaatgacttacaaggcagctgtagatctta
gccacttttaaaagaaaagggggactggaagggctaattcactcccaacgaaaataagatc
tgcttttgcttgtactgggtctctctggttagaccagatctgagcctgggagctctctggct
aactagggaacccactgcttaagcctcaataaagcttgccttgagtgcttcaagtagtgtgtg
cccgtctgttgtgtgactctggtaactagagatccctcagaccctttagtcagtgtggaaaa
tctctagcagtagtagttcatgtcatcttattattcagtatttataacttgcaaagaaatgaa
tatcagagagtgagaggaacttgtttattgcagcttataatggttacaaataaagcaatagca
tcacaaatttcacaaataaagcatttttttcactgcattctagttgtggtttgtccaaactca
tcaatgtatcttatcatgtctggctctagctatcccgcccctaactccgcccagttccgccca
ttctccgccccatggctgactaattttttttatttatgcagaggccgaggccgcctcggcctc
tgagctattccagaagtagtgaggaggctttttggaggcctagacttttgcagagacggccc
aaattcgtaatcatggtcatagctgtttcctgtgtgaaattgttatccgctcacaattccaca
caacatacgagccggaagcataaagtgtaaagcctggggtgcctaatgagtgagctaactcac
attaattgcgttgcgctcactgcccgctttccagtcgggaaacctgtcgtgccagctgcatta
atgaatcggccaacgcgcggggagaggcggtttgcgtattgggcgctcttccgcttcctcgct
cactgactcgctgcgctcggtcgttcggctgcggcgagcggtatcagctcactcaaaggcggt
aatacggttatccacagaatcaggggataacgcaggaaagaacatgtgagcaaaaggccagca
aaaggccaggaaccgtaaaaaggccgcgttgctggcgtttttccataggctccgcccccctga
cgagcatcacaaaaatcgacgctcaagtcagaggtggcgaaacccgacaggactataaagata
ccaggcgtttccccctggaagctccctcgtgcgctctcctgttccgaccctgccgcttaccgg
atacctgtccgcctttctcccttcgggaagcgtggcgctttctcatagctcacgctgtaggta
tctcagttcggtgtaggtcgttcgctccaagctgggctgtgtgcacgaaccccccgttcagcc
cgaccgctgcgccttatccggtaactatcgtcttgagtccaacccggtaagacacgacttatc
gccactggcagcagccactggtaacaggattagcagagcgaggtatgtaggcggtgctacaga
gttcttgaagtggtggcctaactacggctacactagaaggacagtatttggtatctgcgctct
gctgaagccagttaccttcggaaaaagagttggtagctcttgatccggcaaacaaaccaccgc
tggtagcggtggtttttttgtttgcaagcagcagattacgcgcagaaaaaaaggatctcaaga
agatcctttgatcttttctacggggtctgacgctcagtggaacgaaaactcacgttaagggat
tttggtcatgagattatcaaaaaggatcttcacctagatccttttaaattaaaaatgaagttt
taaatcaatctaaagtatatatgagtaaacttggtctgacagttaccaatgcttaatcagtga
ggcacctatctcagcgatctgtctatttcgttcatccatagttgcctgactccccgtcgtgta
gataactacgatacgggagggcttaccatctggccccagtgctgcaatgataccgcgagaccc
acgctcaccggctccagatttatcagcaataaaccagccagccggaagggccgagcgcagaag
tggtcctgcaactttatccgcctccatccagtctattaattgttgccgggaagctagagtaag
tagttcgccagttaatagtttgcgcaacgttgttgccattgctacaggcatcgtggtgtcacg
ctcgtcgtttggtatggcttcattcagctccggttcccaacgatcaaggcg
```

Fig. 8 (Continued)

```
agttacatgatcccccatgttgtgcaaaaaagcggttagctccttcggtcctccgatcgttgt
cagaagtaagttggccgcagtgttatcactcatggttatggcagcactgcataattctcttac
tgtcatgccatccgtaagatgctttctgtgactggtgagtactcaaccaagtcattctgaga
atagtgtatgcggcgaccgagttgctcttgcccggcgtcaatacgggataataccgcgccaca
tagcagaactttaaaagtgctcatcattggaaaacgttcttcggggcgaaaactctcaaggat
cttaccgctgttgagatccagttcgatgtaacccactcgtgcacccaactgatcttcagcatc
ttttactttcaccagcgtttctgggtgagcaaaaacaggaaggcaaaatgccgcaaaaaggg
aataagggcgacacggaaatgttgaatactcatactcttccttttcaatattattgaagcat
ttatcagggttattgtctcatgagcggatacatatttgaatgtatttagaaaaataaacaaat
agggggttccgcgcacatttccccgaaaagtgccacctgacgtctaagaaaccattattatcat
gacattaacctataaaaataggcgtatcacgaggcccttcgtctcgcgcgtttcggtgatga
cggtgaaaacctctgacacatgcagctcccggagacggtcacagcttgtctgtaagcggatgc
cgggagcagacaagcccgtcagggcgcgtcagcgggtgttggcgggtgtcggggctggcttaa
ctatgcggcatcagagcagattgtactgagagtgcaccatatgcggtgtgaaataccgcacag
atgcgtaaggagaaaataccgcatcaggcgccattcgccattcaggctgcgcaactgttggga
agggcgatcggtgcgggcctcttcgctattacgccagctggcgaaaggggatgtgctgcaag
gcgattaagttgggtaacgccagggttttcccagtcacgacgttgtaaaacgacggccagtgc
caagctg
```

Fig. 8 (Continued)

```
First pair of primers to get NheI-wtTNFRGDC-NotIfragment
SEQ ID No.: 2
NheI-wtTNF-S:
CTAGCTAGCATGAGCACTGAAAGCATGATCCGGGAC
SEQ ID No.: 3
NotI-RGDCwtTNF-AS:
AAGGAAAAAAGCGGCCGCTCAGCAAAAGCAATCACCACGGCAATCGCACAGGGC Second pair of primers to get pacI-mrfp-ttk-XhoI fragment
SEQ ID No.: 4
PacI-rfp-tk-S:
CCTTAATTAAATGCGCTTCAAGGTGCGCATGGAG
SEQ ID No.: 5
XhoI-rfp-tk-AS:
CCGCTCGAGTCAGTTAGCCTCCCCCATCTCCCGG
```

Fig. 9

SEQ ID No.: 6
GAAAGGACACCATGAGCACTGAAAGCATGATCCGGGACGTGGAGCTGGCCGAGGAGGCGCTCC
CCAAGAAGACAGGGGGGCCCCAGGGCTCCAGGCGGTGCTTGTTCCTCAGCCTCTTCTCCTTCC
TGATCGTGGCAGGCGCCACCACGCTCTTCTGCCTGCTGCACTTTGGAGTGATCGGCCCCCAGA
GGGAAGAGTTCCCCAGGGACCTCTCTCTAATCAGCCCTCTGGCCCAGGCAGTCAGATCATCTT
CTCGAACCCCGAGTGACAAGCCTGTAGCCCATGTTGTAGCAAACCCTCAAGCTGAGGGGCAGC
TCCAGTGGCTGAACCGCCGGGCCAATGCCCTCCTGGCCAATGGCGTGGAGCTGAGAGATAACC
AGCTGGTGGTGCCATCAGAGGGCCTGTACCTCATCTACTCCCAGGTCCTCTTCAAGGGCCAAG
GCTGCCCCTCCACCCATGTGCTCCTCACCCACACCATCAGCCGCATCGCCGTCTCCTACCAGA
CCAAGGTCAACCTCCTCTCTGCCATCAAGAGCCCCTGCCAGAGGGAGACCCCAGAGGGGGCTG
AGGCCAAGCCCTGGTATGAGCCCATCTATCTGGGAGGGGTCTTCCAGCTGGAGAAGGGTGACC
GACTCAGCGCTGAGATCAATCGGCCCGACTATCTCGACTTTGCCGAGTCTGGGCAGGTCTACT
TTGGGATCATTGCCCTGTGAGG

*Fig. 10*

SEQ ID No.: 7
ATGGCTTCCAAGGTGTACGACCCCGAGCAACGCAAACGCATGATCACTGGGCCTCAGTGGTGG
GCTCGCTGCAAGCAAATGAACGTGCTGGACTCCTTCATCAACTACTATGATTCCGAGAAGCAC
GCCGAGAACGCCGTGATTTTTCTGCATGGTAACGCTGCCTCCAGCTACCTGTGGAGGCACGTC
GTGCCTCACATCGAGCCCGTGGCTAGATGCATCATCCCTGATCTGATCGGAATGGGTAAGTCC
GGCAAGAGCGGGAATGGCTCATATCGCCTCCTGGATCACTACAAGTACCTCACCGCTTGGTTC
GAGCTGCTGAACCTTCCAAAGAAAATCATCTTTGTGGGCCACGACTGGGGGGCTTGTCTGGCC
TTTCACTACTCCTACGAGCACCAAGACAAGATCAAGGCCATCGTCCATGCTGAGAGTGTCGTG
GACGTGATCGAGTCCTGGGACGAGTGGCCTGACATCGAGGAGGATATCGCCCTGATCAAGAGC
GAAGAGGGCGAGAAAATGGTGCTTGAGAATAACTTCTTCGTCGAGACCATGCTCCCAAGCAAG
ATCATGCGGAAACTGGAGCCTGAGGAGTTCGCTGCCTACCTGGAGCCATTCAAGGAGAAGGGC
GAGGTTAGACGGCCTACCCTCTCCTGGCCTCGCGAGATCCCTCTCGTTAAGGGAGGCAAGCCC
GACGTCGTCCAGATTGTCCGCAACTACAACGCCTACCTTCGGGCCAGCGACGATCTGCCTAAG
ATGTTCATCGAGTCCGACCCTGGGTTCTTTTCCAACGCTATTGTCGAGGGAGCTAAGAAGTTC
CCTAACACCGAGTTCGTGAAGGTGAAGGGCCTCCACTTCAGCCAGGAGGACGCTCCAGATGAA
ATGGGTAAGTACATCAAGAGCTTCGTGGAGCGCGTGCTGAAGAACGAGCAGCTCGAGAATTCT
CACGCGTCTGCAGGATATCAAGCTTCCACCATGGCCTCCTCCGAGGACGTCATCAAGGAGTTC
ATGCGCTTCAAGGTGCGCATGGAGGGCTCCGTGAACGGCCACGAGTTCGAGATCGAGGGCGAG
GGCGAGGGCCGCCCCTACGAGGGCACCCAGACCGCCAAGCTGAAGGTGACCAAGGGCGGCCCC
CTGCCCTTCGCCTGGGACATCCTGTCCCCTCAGTTCCAGTACGGCTCCAAGGCCTACGTGAAG
CACCCCGCCGACATCCCCGACTACTTGAAGCTGTCCTTCCCCGAGGGCTTCAAGTGGGAGCGC
GTGATGAACTTCGAGGACGGCGGCGTGGTGACCGTGACCCAGGACTCCTCCCTGCAGGACGGC
GAGTTCATCTACAAGGTGAAGCTGCGCGGCACCAACTTCCCCTCCGACGGCCCCGTAATGCAG
AAGAAGACCATGGGCTGGGAGGCCTCCACCGAGCGGATGTACCCCGAGGACGGCGCCCTGAAG
GGCGAGATCAAGATGAGGCTGAAGCTGAAGGACGGCGGCCACTACGACGCCGAGGTCAAGACC
ACCTACATGGCCAAGAAGCCCGTGCAGCTGCCCGGCGCCTACAAGACCGACATCAAGCTGGAC
ATCACCTCCCACAACGAGGACTACACCATCGTGGAACAGTACGAGCGCGCCGAGGGCCGCCAC
TCCACCGGCGCCACCGCGGGCCCGGGATCCGCCACCATGCCCACGCTACTGCGGGTTTATATA
GACGGTCCCCACGGGATGGGGAAAACCACCACCACCACGCAACTGCTGGTGGCCCTGGGTTCG
CGCGACGATATCGTCTACGTACCCGAGCCGATGACTTACTGGCGGGTGCTGGGGGCTTCCGAG
ACAATCGCGAACATCTACACCACACAACACCGCCTCGACCAGGGTGAGATATCGGCCGGGGAC
GCGGCGGTGGTAATGACAAGCGCCCAGATAACAATGCCTTATGCCGTGACCGACGCCGTTCTG
GCTCCTCATATCGGGGGGGAGGCTGGGAGCTCACATGCCCCGCCCCCGGCCCTCACCATCTTC
CTCGACCGCCATCCCATCGCCTTCATGCTGTGCTACCCGGCCGCGCGGTACCTTATGGGCAGC
ATGACCCCCCAGGCCGTGCTGGCGTTCGTGGCCCTCATCCCGCCGACCTTGCCCGGCACCAAC
ATCGTGCTTGGGGCCCTTCCGGAGGACAGACACATCGACCGCCTGGCCAAACGCCAGCGCCCC
GGCGAGCGGCTGGACCTGGCTATGCTGGCTGCGATTCGCCGCGTTTACGGGCTACTTGCCAAT
ACGGTGCGGTATCTGCAGTGCGGCGGGTCGTGGCGGGAGGACTGGGGACAGCTTTCGGGGACG
GCCGTGCCGCCCCAGGGTGCCGAGCCCCAGAGCAACGCGGGCCCACGACCCCATATCGGGGAC
ACGTTATTTACCCTGTTTCGGGCCCCCGAGTTGATGGCCCCCAACGGCGACCTGTATAACGTG
TTTGCCTGGGCCTTGGACGTCTTGGCCAAACGCCTCCGTTCCATGACGTCTTTATCCTGGAT
TACGACCAATCGCCCGCCGGCTGCCGGGACGCCCTGCTGCAACTTACCTCCGGGATGGTCCAG
ACCCACGTCACCACCCCCGGCTCCATACCGACGATATGCGACCTGGCGCGCACGTTT
GCCCGGGAGATGGGGGAGGCTAACTGA

*Fig. 11*

SEQ ID NO.: 9
MIRDVELAEEALPKKTGGPQGSRRCLFLSLFSFLIVAGATTLFCLLHFGVIGPQREEFPRDL
SLISPLAQAVRSSSRTPSDKPVAHVVANPQAEGQLQWLNRRANALLANGVELRDNQLVVPSE
GLYLIYSQVLFKGQGCPSTHVLLTHTISRIAVSYQTKVNLLSAIKSPCQRETPEGAEAKPWY
EPIYLGGVFQLEKGDRLSAEINRPDYLDFAESGQVYFGIIAL

*Fig. 12*

SEQ ID NO.: 10
IRDVELAEEALPKKTGGPQGSRRCLFLSLFSFLIVAGATTLFCLLHFGVIGPQREEFPRDLS
LISPLAQAVRSSSRTPSDKPVAHVVANPQAEGQLQWLNRRANALLANGVELRDNQLVVPSEG
LYLIYSQVLFKGQGCPSTHVLLTHTISRIAVSYQTKVNLLSAIKSPCQRETPEGAEAKPWYE
PIYLGGVFQLEKGDRLSAEINRPDYLDFAESGQVYFGIIALCDCRGDCFC

*Fig. 13*

SEQ ID NO.: 11
atccgggacgtggagctggccgaggaggcgctccccaagaagacagggggggccccagggctc
caggcggtgcttgttcctcagcctcttctccttcctgatcgtggcaggcgccaccacgctct
tctgcctgctgcactttggagtgatcggcccccagagggaagagttccccagggacctctct
ctaatcagccctctggcccaggcagtcagatcatcttctcgaaccccgagtgacaagcctgt
agcccatgttgtagcaaaccctcaagctgaggggcagctccagtggctgaaccgccgggcca
atgccctcctggccaatggcgtggagctgagagataaccagctggtggtgccatcagagggc
ctgtacctcatctactcccaggtcctcttcaagggccaaggctgcccctccacccatgtgct
cctcacccacaccatcagccgcatcgccgtctcctaccagaccaaggtcaacctcctctctg
ccatcaagagcccctgccagagggagacccagagggggctgaggccaagccctggtatgag
cccatctatctgggaggggtcttccagctggagaagggtgaccgactcagcgctgagatcaa
tcggcccgactatctcgactttgccgagtctgggcaggtctactttgggatcattgccctg

*Fig. 14*

SEQ ID NO.: 12
atccgggacgtggagctggccgaggaggcgctccccaagaagacagggggggccccagggctcc
aggcggtgcttgttcctcagcctcttctccttcctgatcgtggcaggcgccaccacgctcttc
tgcctgctgcactttggagtgatcggcccccagagggaagagttccccagggacctctctcta
atcagccctctggcccaggcagtcagatcatcttctcgaaccccgagtgacaagcctgtagcc
catgttgtagcaaaccctcaagctgaggggcagctccagtggctgaaccgccgggccaatgcc
ctcctggccaatggcgtggagctgagagataaccagctggtggtgccatcagagggcctgtac
ctcatctactcccaggtcctcttcaagggccaaggctgcccctccacccatgtgctcctcacc
cacaccatcagccgcatcgccgtctcctaccagaccaaggtcaacctcctctctgccatcaag
agcccctgccagagggagacccagagggggctgaggccaagccctggtatgagcccatctat
ctgggaggggtcttccagctggagaagggtgaccgactcagcgctgagatcaatcggcccgac
tatctcgactttgccgagtctgggcaggtctactttgggatcattgccctgtgcgattgccgt
ggtgattgcttttgc

*Fig. 15*

SEQUENCE LISTING

```
<160> NUMBER OF SEQ ID NOS: 12

<210> SEQ ID NO 1
<211> LENGTH: 9232
<212> TYPE: DNA
<213> ORGANISM: Artificial sequence
<220> FEATURE:
<223> OTHER INFORMATION: Lentiviral vector pCDH-MSCV-hTNF-RGD4C-EF1-
      mrfp-ttk.str

<400> SEQUENCE: 1
acgcgtgtag tcttatgcaa tactcttgta gtcttgcaac atggtaacga tgagttagca        60
acatgcctta caaggagaga aaaagcaccg tgcatgccga ttggtggaag taaggtggta       120
cgatcgtgcc ttattaggaa ggcaacagac gggtctgaca tggattggac gaaccactga       180
attgccgcat tgcagagata ttgtatttaa gtgcctagct cgatacaata aacgggtctc       240
tctggttaga ccagatctga gcctgggagc tctctggcta actagggaac ccactgctta       300
agcctcaata aagcttgcct tgagtgcttc aagtagtgtg tgcccgtctg ttgtgtgact       360
ctggtaacta gagatccctc agaccctttt agtcagtgtg gaaaatctct agcagtggcg       420
cccgaacagg gacctgaaag cgaaagggaa accagagctc tctcgacgca ggactcggct       480
tgctgaagcg cgcacggcaa gaggcgaggg gcggcgactg tgagtacgc caaaaatttt        540 gactagcgga ggctagaagg agagagatgg gtgcgagagc gtcagtatta agcggggag        600 aattagatcg cgatgggaaa aaattcggtt aaggccaggg ggaagaaaa aatataaatt        660 aaaacatata gtatgggcaa gcagggagct agaacgattc gcagttaatc ctggcctgtt       720
agaaacatca gaaggctgta gacaaatact gggacagcta caaccatccc ttcagacagg       780
atcagaagaa cttagatcat tatataatac agtagcaacc ctctattgtg tgcatcaaag       840
gatagagata aaagacacca aggaagcttt agacaagata gaggaagagc aaaacaaaag       900
taagaccacc gcacagcaag cggccactga tcttcagacc tggaggagga gatatgaggg       960
acaattggag aagtgaatta tataaatata agtagtaaa aattgaacca ttaggagtag      1020
cacccaccaa ggcaaagaga agagtggtgc agagagaaaa aagagcagtg ggaataggag     1080
ctttgttcct tgggttcttg ggagcagcag gaagcactat gggcgcagcc tcaatgacgc     1140
tgacggtaca ggccagacaa ttattgtctg gtatagtgca gcagcagaac aatttgctga     1200
gggctattga ggcgcaacag catctgttgc aactcacagt ctggggcatc aagcagctcc     1260
aggcaagaat cctggctgtg gaaagatacc taaaggatca acagctcctg gggatttggg     1320
gttgctctgg aaaactcatt tgcaccactg ctgtgccttg gaatgctagt tggagtaata     1380
aatctctgga acagattgga atcacacgac ctggatggag tgggacagag aaattaacaa     1440
```

```
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct  gtactttcta tagtgaatag agttaggcag ggatattcac cattatcgtt     1680
tcagacccac ctcccaaccc cgaggggacc cgacaggccc gaaggaatag aagaagaagg    1740
tggagagaga gacagagaca gatccattcg attagtgaac ggatctcgac ggttaacttt    1800
taaaagaaaa ggggggattg ggggtacag tgcaggggaa agaatagtag acataatagc     1860
aacagacata caaactaaag aattacaaaa acaaattaca aaaattcaaa attttatcga    1920
tactagttga aagaccccac ctgtaggttt ggcaagttag cttaagtaac gccattttgc    1980
aaggcatgga aaatacataa ctgagaatag agaagttcag atcaaggtta ggaacagaga    2040
gacagcagaa tatgggccaa acaggatatc tgtggtaagc agttcctgcc ccggctcagg    2100
gccaagaaca gatggtcccc agatgcggtc ccgccctcag cagtttctag cgaaccatca    2160 gatgttcca gggtgcccca aggacctgaa atgaccctgt gccttatttg aactaaccaa     2220 tcagttgct tcttgcttct gtttgtgtgc ttctgctccc tgagctcaat aaaagagccc      2280
acaacccctc acttggtggg ccagtcctct gatagactgt gtcccctgga tacccgtatt    2340
ctagagctag catgagcact gaaagcatga tccgggacgt ggagctggcc gaggaggcgc    2400
tccccaagaa gacaggggg ccccagggct ccaggcggtg cttgttcctc agcctcttct      2460
ccttcctgat cgtggcaggc gccaccacgc tcttctgcct gctgcacttt ggagtgatcg    2520
gcccccagag ggaagagttc cccagggacc tctctctaat cagccctctg gcccaggcag   2580
tcagatcatc ttctcgaacc ccgagtgaca agcctgtagc ccatgttgta gcaaaccctc    2640
aagctgaggg gcagctccag tggctgaacc gccgggccaa tgccctcctg gccaatggcg    2700
tggagctgag agataaccag ctggtggtgc catcagaggg cctgtacctc atctactccc    2760
aggtcctctt caagggccaa ggctgcccct ccacccatgt gctcctcacc cacaccatca   2820
gccgcatcgc cgtctcctac cagaccaagg tcaacctcct ctctgccatc aagagcccct    2880
gccagaggga gaccccagag ggggctgagg ccaagccctg gtatgagccc atctatctgg    2940
gagggtcctt ccagctggag aagggtgacc gactcagcgc tgagatcaat cggcccgact   3000
atctcgactt tgccgagtct gggcaggtct actttgggat cattgccctg tgcgattgcc    3060
gtggtgattg cttttgctga gcggccgcaa ggatctgcga tcgctccggt gcccgtcagt    3120
gggcagagcg cacatcgccc acagtccccg agaagttggg gggaggggtc ggcaattgaa    3180
cgggtgccta gagaaggtgg cgcggggtaa actgggaaag tgatgtcgtg tactggctcc    3240 gccttttcc cgagggtggg ggagaaccgt atataagtgc agtagtcgcc gtgaacgttc      3300
tttttcgcaa cgggtttgcc gccagaacac agctgaagct tcgaggggct cgcatctctc    3360
cttcacgcgc ccgccgccct acctgaggcc gccatccacg ccggttgagt cgcgttctgc    3420
cgcctcccgc ctgtggtgcc tcctgaactg cgtccgccgt ctaggtaagt ttaaagctca   3480
ggtcgagacc gggcctttgt ccggcgctcc cttggagcct acctagactc agccggctct    3540
ccacgctttg cctgacccctg cttgctcaac tctacgtctt tgtttcgttt tctgttctgc    3600
gccgttacag atccaagctg tgaccggcgc ctacgctaga cgccaccttta attaaatgcg  3660 cttcaaggtg cgcatggagg gctccgtgaa cggccacgag ttcgagatcg agggcgaggg    3720
cgagggccgc ccctacgagg gcacccagac cgccaagctg aaggtgacca agggcggccc   3780
cctgcccttc gcctgggaca tcctgtcccc tcagttccag tacggctcca aggcctacgt    3840
```

```
gaagcacccc gccgacatcc ccgactactt gaagctgtcc ttccccgagg gcttcaagtg    3900
ggagcgcgtg atgaacttcg aggacggcgg cgtggtgacc gtgacccagg actcctccct    3960
gcaggacggc gagttcatct acaaggtgaa gctgcgcggc accaacttcc cctccgacgg    4020
ccccgtaatg cagaagaaga ccatgggctg ggaggcctcc accgagcgga tgtaccccga    4080
ggacggcgcc ctgaagggcg agatcaagat gaggctgaag ctgaaggacg gcggccacta    4140
cgacgccgag gtcaagacca cctacatggc caagaagccc gtgcagctgc ccggcgccta    4200
caagaccgac atcaagctgg acatcacctc ccacaacgag gactacacca tcgtggaaca    4260
gtacgagcgc gccgagggcc gccactccac cggcgccacc gcgggcccgg gatccgccac    4320
catgcccacg ctactgcggg tttatataga cggtccccac gggatgggga aaaccaccac    4380
caccacgcaa ctgctggtgg ccctgggttc gcgcgacgat atcgtctacg tacccgagcc    4440
gatgacttac tggcgggtgc tggggcttc cgagacaatc gcgaacatct acaccacaca    4500
acaccgcctc gaccagggtg agatatcggc cgggacgcg cgtggtaa tgacaagcgc    4560 ccagataaca atgccttatg ccgtgaccga cgccgttctg gctcctcata tcgggggga    4620 ggctgggagc tcacatgccc cgcccccggc cctcaccatc ttcctcgacc gccatcccat    4680
cgccttcatg ctgtgctacc cggccgcgcg gtaccttatg gcagcatga ccccccaggc    4740 cgtgctggcg ttcgtggccc tcatcccgcc gaccttgccc ggcaccaaca tcgtgcttgg    4800
ggcccttccg gaggacagac acatcgaccg cctggccaaa cgccagcgcc ccggcgagcg    4860
gctggacctg gctatgctgg ctgcgattcg ccgcgtttac gggctacttg ccaatacggt    4920
gcggtatctg cagtgcggcg gtcgtggcg ggaggactgg ggacagcttt cggggacggc    4980
cgtgccgccc cagggtgccg agccccgag caacgcgggc ccacgacccc atatcgggga    5040
cacgttattt accctgtttc gggccccga gttgatggcc cccaacggcg acctgtataa    5100
cgtgtttgcc tgggccttgg acgtcttggc caaacgcctc cgttccatgc acgtctttat    5160
cctggattac gaccaatcgc ccgccggctg ccggacgcc ctgctgcaac ttacctccgg    5220
gatggtccag acccacgtca ccacccccgg ctccataccg acgatatgcg acctggcgcg    5280
cacgtttgcc cgggagatgg gggaggctaa ctgactcgag gtcgacaatc aacctctgga    5340
ttacaaaatt tgtgaaagat tgactggtat tcttaactat gttgctcctt ttacgctatg    5400
tggatacgct gctttaatgc cttttgatcta tgctattgct tcccgtatgg ctttcatttt    5460
ctcctccttg tataaatcct ggttgctgtc tctttatgag gagttgtggc ccgttgtcag    5520
gcaacgtggc gtggtgtgca ctgtgtttgc tgacgcaacc cccactggtt ggggcattgc    5580
caccacctgt cagctccttt ccgggacttt cgctttcccc ctccctattg ccacggcgga    5640
actcatcgcc gcctgccttg cccgctgctg acagggggct cggctgttgg cactgacaa    5700 ttccgtggtg ttgtcgggga atcatcgtc ctttccttgg ctgctcgcct gtgttgccac    5760
ctggattctg cgcgggacgt ccttctgcta cgtcccttcg ccctcaatc cagcggacct    5820 tccttcccgc ggcctgctgc cggctctgcg gcctcttccg cgtcttcgcc ttcgccctca    5880
gacgagtcgg atctcccttt gggccgcctc ccgcctggt acctttaaga ccaatgactt    5940
acaaggcagc tgtagatctt agccactttt taaaagaaaa ggggggactg aagggctaa     6000 ttcactccca acgaaaataa gatctgcttt ttgcttgtac tgggtctctc tggttagacc    6060
agatctgagc ctgggagctc tctggctaac taggaaccc actgcttaag cctcaataaa    6120
gcttgccttg agtgcttcaa gtagtgtgtg cccgtctgtt gtgtgactct ggtaactaga    6180
```

```
gatccctcag acccttttag tcagtgtgga aatctctag cagtagtagt tcatgtcatc    6240
ttattattca gtatttataa cttgcaaaga aatgaatatc agagagtgag aggaacttgt    6300
ttattgcagc ttataatggt tacaaataaa gcaatagcat cacaaatttc acaaataaag    6360 cattttttc actgcattct agttgtggtt tgtccaaact catcaatgta tcttatcatg     6420
tctggctcta gctatcccgc ccctaactcc gcccagttcc gcccattctc cgccccatgg    6480
ctgactaatt tttttatttt atgcagaggc cgaggccgcc tcggcctctg agctattcca    6540
gaagtagtga ggaggcttt ttggaggcct agacttttgc agagacggcc caaattcgta     6600
atcatggtca tagctgtttc ctgtgtgaaa ttgttatccg ctcacaattc cacacaacat    6660
acgagccgga agcataaagt gtaaagcctg gggtgcctaa tgagtgagct aactcacatt    6720
aattgcgttg cgctcactgc ccgctttcca gtcgggaaac ctgtcgtgcc agctgcatta    6780
atgaatcggc caacgcgcgg ggagaggcgg tttgcgtatt gggcgctctt ccgcttcctc    6840
gctcactgac tcgctgcgct cggtcgttcg gctgcggcga gcggtatcag ctcactcaaa    6900
ggcggtaata cggttatcca cagaatcagg ggataacgca ggaaagaaca tgtgagcaaa    6960
aggccagcaa aaggccagga accgtaaaaa ggccgcgttg ctggcgtttt tccataggct    7020
ccgcccccct gacgagcatc acaaaaatcg acgctcaagt cagaggtggc gaaacccgac    7080
aggactataa agataccagg cgtttccccc tggaagctcc ctcgtgcgct ctcctgttcc    7140
gaccctgccg cttaccggat acctgtccgc ctttctccct tcgggaagcg tggcgctttc    7200
tcatagctca cgctgtaggt atctcagttc ggtgtaggtc gttcgctcca agctgggctg    7260
tgtgcacgaa ccccccgttc agcccgaccg ctgcgcctta tccggtaact atcgtcttga    7320
gtccaacccg gtaagacacg acttatcgcc actggcagca gccactggta acaggattag    7380
cagagcgagg tatgtaggcg gtgctacaga gttcttgaag tggtggccta actacggcta    7440
cactagaagg acagtatttg gtatctgcgc tctgctgaag ccagttacct tcggaaaaag    7500
agttggtagc tcttgatccg gcaaacaaac caccgctggt agcggtggtt tttttgtttg    7560
caagcagcag attacgcgca gaaaaaaagg atctcaagaa gatcctttga tcttttctac    7620
ggggtctgac gctcagtgga acgaaaactc acgttaaggg attttggtca tgagattatc    7680
aaaaaggatc ttcacctaga tccttttaaa ttaaaaatga agttttaaat caatctaaag    7740
tatatatgag taaacttggt ctgacagtta ccaatgctta atcagtgagg cacctatctc    7800
agcgatctgt ctatttcgtt catccatagt tgcctgactc ccgtcgtgt agataactac      7860 gatacgggag ggcttaccat ctggccccag tgctgcaatg ataccgcgag acccacgctc    7920
accggctcca gatttatcag caataaacca gccagccgga agggccgagc gcagaagtgg    7980
tcctgcaact ttatccgcct ccatccagtc tattaattgt tgccgggaag ctagagtaag    8040
tagttcgcca gttaatagtt tgcgcaacgt tgttgccatt gctacaggca tcgtggtgtc    8100
acgctcgtcg tttggtatgg cttcattcag ctccggttcc caacgatcaa ggcgagttac    8160
atgatccccc atgttgtgca aaaaagcggt tagctccttc ggtcctccga tcgttgtcag    8220
aagtaagttg gccgcagtgt tatcactcat ggttatggca gcactgcata attctcttac    8280
tgtcatgcca tccgtaagat gcttttctgt gactggtgag tactcaacca agtcattctg    8340
agaatagtgt atgcggcgac cgagttgctc ttgcccggcg tcaatacggg ataataccgc    8400
gccacatagc agaactttaa aagtgctcat cattggaaaa cgttcttcgg ggcgaaaact    8460
ctcaaggatc ttaccgctgt tgagatccag ttcgatgtaa cccactcgtg cacccaactg    8520
atcttcagca tcttttactt tcaccagcgt ttctgggtga gcaaaaacag gaaggcaaaa    8580
```

```
tgccgcaaaa aagggaataa gggcgacacg gaaatgttga atactcatac tcttcctttt    8640
tcaatattat tgaagcattt atcagggtta ttgtctcatg agcggataca tatttgaatg    8700
tatttagaaa aataaacaaa tagggttcc gcgcacattt ccccgaaaag tgccacctga     8760
cgtctaagaa accattatta tcatgacatt aacctataaa aataggcgta tcacgaggcc    8820
ctttcgtctc gcgcgtttcg gtgatgacgg tgaaaacctc tgacacatgc agctcccgga    8880
gacggtcaca gcttgtctgt aagcggatgc cgggagcaga caagcccgtc agggcgcgtc    8940
agcgggtgtt ggcgggtgtc ggggctggct taactatgcg gcatcagagc agattgtact    9000
gagagtgcac catatgcggt gtgaaatacc gcacagatgc gtaaggagaa ataccgcat     9060 caggcgccat tcgccattca ggctgcgcaa ctgttgggaa gggcgatcgg tgcgggcctc    9120
ttcgctatta cgccagctgg cgaaagggg  atgtgctgca aggcgattaa gttgggtaac    9180
gccagggttt tcccagtcac gacgttgtaa aacgacggcc agtgccaagc tg            9232

<210> SEQ ID NO 2
<211> LENGTH: 36
<212> TYPE: DNA
<213> ORGANISM: Artificial sequence
<220> FEATURE:
<223> OTHER INFORMATION: Primer NheI-wtTNF-S for NheI-wtTNFRGDC-NotI
      fragment

<400> SEQUENCE: 2
ctagctagca tgagcactga aagcatgatc cgggac                               36

<210> SEQ ID NO 3
<211> LENGTH: 54
<212> TYPE: DNA
<213> ORGANISM: Artificial sequence
<220> FEATURE:
<223> OTHER INFORMATION: Primer NotI-RGDCwtTNF-AS for NheI-wtTNFRGDC-
      NotI fragment

<400> SEQUENCE: 3
aaggaaaaaa gcggccgctc agcaaaagca atcaccacgg caatcgcaca gggc           54

<210> SEQ ID NO 4
<211> LENGTH: 34
<212> TYPE: DNA
<213> ORGANISM: Artificial sequence
<220> FEATURE:
<223> OTHER INFORMATION: Primer PacI-rfp-tk-s for pacI-mrfp-ttk-XhoI
      fragment

<400> SEQUENCE: 4
ccttaattaa atgcgcttca aggtgcgcat ggag                                 34

<210> SEQ ID NO 5
<211> LENGTH: 34
<212> TYPE: DNA
<213> ORGANISM: Artificial sequence
<220> FEATURE:
<223> OTHER INFORMATION: Primer XhoI-rfp-tk-AS for pacI-mrfp-ttk-XhoI
      fragment

<400> SEQUENCE: 5
ccgctcgagt cagttagcct ccccatctc ccgg                                  34

<210> SEQ ID NO 6
<211> LENGTH: 715
<212> TYPE: DNA
```

<213> ORGANISM: Artificial sequence
<220> FEATURE:
<223> OTHER INFORMATION: Template for NheI-wtTNFRGD4C-NotI fragmnet

<400> SEQUENCE: 6

```
gaaaggacac catgagcact gaaagcatga tccgggacgt ggagctggcc gaggaggcgc      60
tccccaagaa gacagggggg ccccagggct ccaggcggtg cttgttcctc agcctcttct     120
ccttcctgat cgtggcaggc gccaccacgc tcttctgcct gctgcacttt ggagtgatcg     180
gcccccagag ggaagagttc cccagggacc tctctctaat cagccctctg cccaggcag      240
tcagatcatc ttctcgaacc ccgagtgaca agcctgtagc ccatgttgta gcaaaccctc     300
aagctgaggg gcagctccag tggctgaacc gccgggccaa tgcccctg gccaatggcg       360
tggagctgag agataaccag ctggtggtgc atcagaggg cctgtacctc atctactccc      420
aggtcctctt caagggccaa ggctgcccct ccacccatgt gctcctcacc cacaccatca     480
gccgcatcgc cgtctcctac cagaccaagg tcaacctcct ctctgccatc aagagcccct    540
gccagaggga gacccccagag ggggctgagg ccaagccctg gtatgagccc atctatctgg    600
gaggggtctt ccagctggag aagggtgacc gactcagcgc tgagatcaat cggcccgact    660
atctcgactt tgccgagtct gggcaggtct actttgggat cattgccctg tgagg          715
```

<210> SEQ ID NO 7
<211> LENGTH: 2667
<212> TYPE: DNA
<213> ORGANISM: Artificial sequence
<220> FEATURE:
<223> OTHER INFORMATION: Nucleic acid sequence of template for
      generating PacI-mrfp-ttk-XhoI fragment

<400> SEQUENCE: 7

```
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gattttctg catggtaacg ctgcctccag ctacctgtgg     180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tgggggggctt gtctggcctt tcactactcc tacgagcacc aagacaagat caaggccatc   420
gtccatgctg agagtgtcgt ggacgtgatc gagtcctggg acgagtggcc tgacatcgag   480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct   600
gcctacctgg agccattcaa ggagaagggc gaggttagac ggcctaccct ctcctggcct    660
cgcgagatcc ctctcgttaa gggaggcaag cccgacgtcg tccagattgt ccgcaactac   720
aacgcctacc ttcgggccag cgacgatctg cctaagatgt tcatcgagtc cgaccctggg   780
ttctttttcca acgctattgt cgagggagct aagaagttcc ctaacaccga gttcgtgaag   840
gtgaagggcc tccacttcag ccaggaggac gctccagatg aaatgggtaa gtacatcaag   900
agcttcgtgg agcgcgtgct gaagaacgag cagctcgaga ttctcacgc gtctgcagga    960
tatcaagctt ccaccatggc ctcctccgag gacgtcatca aggagttcat gcgcttcaag   1020
gtgcgcatgg agggctccgt gaacggccac gagttcgaga tcgagggcga gggcgagggc   1080
cgcccctacg agggcaccca gaccgccaag ctgaaggtga ccaagggcgg ccccctgccc   1140
```

```
ttcgcctggg acatcctgtc ccctcagttc cagtacggct ccaaggccta cgtgaagcac    1200
cccgccgaca tccccgacta cttgaagctg tccttccccg agggcttcaa gtgggagcgc    1260
gtgatgaact tcgaggacgg cggcgtggtg accgtgaccc aggactcctc cctgcaggac    1320
ggcgagttca tctacaaggt gaagctgcgc ggcaccaact tccccctccga cggccccgta    1380
atgcagaaga agaccatggg ctgggaggcc tccaccgagc ggatgtaccc cgaggacggc    1440
gccctgaagg gcgagatcaa gatgaggctg aagctgaagg acggcggcca ctacgacgcc    1500
gaggtcaaga ccacctacat ggccaagaag cccgtgcagc tgcccggcgc ctacaagacc    1560
gacatcaagc tggacatcac ctcccacaac gaggactaca ccatcgtgga acagtacgag    1620
cgcgccgagg gccgccactc caccggcgcc accgcgggcc cgggatccgc caccatgccc    1680
acgctactgc gggtttatat agacggtccc cacgggatgg ggaaaaccac caccaccacg    1740
caactgctgg tggccctggg ttcgcgcgac gatatcgtct acgtacccga gccgatgact    1800
tactggcggg tgctggggc ttccgagaca atcgcgaaca tctacaccac acaacaccgc    1860
ctcgaccagg gtgagatatc ggccggggac gcggcggtgg taatgacaag cgcccagata    1920
acaatgcctt atgccgtgac cgacgccgtt ctggctcctc atatcggggg ggaggctggg    1980
agctcacatg ccccgccccc ggccctcacc atcttcctcg accgccatcc catcgccttc    2040
atgctgtgct acccggccgc gcggtacctt atgggcagca tgacccccca ggccgtgctg    2100
gcgttcgtgg ccctcatccc gccgaccttg cccggcacca catcgtgct ggggccctt    2160
ccggaggaca gacacatcga ccgcctggcc aaacgccagc gccccggcga gcggctggac    2220
ctggctatgc tggctgcgat tcgccgcgtt tacgggctac ttgccaatac ggtgcggtat    2280
ctgcagtgcg gcgggtcgtg gcgggaggac tggggacagc tttcggggac ggccgtgccg    2340
ccccaggtg ccgagcccca gagcaacgcg ggccccacgac cccatatcgg ggacacgtta    2400
tttaccctgt ttcgggcccc cgagttgatg gcccccaacg gcgacctgta taacgtgttt    2460
gcctgggcct tggacgtctt ggccaaacgc ctccgttcca tgcacgtctt tatcctggat    2520
tacgaccaat cgcccgccgg ctgccgggac gccctgctgc aacttacctc cgggatggtc    2580
cagacccacg tcaccacccc cggctccata ccgacgatat cgacctggc gcgcacgttt    2640
gcccgggaga tggggggggc taactga                                       2667

<210> SEQ ID NO 8
<211> LENGTH: 9
<212> TYPE: PRT
<213> ORGANISM: Artificial sequence
<220> FEATURE:
<223> OTHER INFORMATION: RGD4C region

<400> SEQUENCE: 8

Cys Asp Cys Arg Gly Asp Cys Phe Cys
1               5

<210> SEQ ID NO 9
<211> LENGTH: 233
<212> TYPE: PRT
<213> ORGANISM: Artificial sequence
<220> FEATURE:
<223> OTHER INFORMATION: TNF fragment

<400> SEQUENCE: 9

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
```

```
            20                  25                  30
Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 10
<211> LENGTH: 242
<212> TYPE: PRT
<213> ORGANISM: Artificial sequence
<220> FEATURE:
<223> OTHER INFORMATION: TNFRGD4C fusion polypeptide

<400> SEQUENCE: 10

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
```

```
145                 150                 155                 160
Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu Cys Asp Cys Arg Gly Asp Cys
225                 230                 235                 240

Phe Cys

<210> SEQ ID NO 11
<211> LENGTH: 699
<212> TYPE: DNA
<213> ORGANISM: Artificial sequence
<220> FEATURE:
<223> OTHER INFORMATION: Nucleic acid sequence encoding amino acid
      sequence of TNF fragment

<400> SEQUENCE: 11
atgagcactg aaagcatgat ccgggacgtg gagctggccg aggaggcgct ccccaagaag        60 acagggggc cccagggctc caggcggtgc ttgttcctca gcctcttctc cttcctgatc       120
gtggcaggcg ccaccacgct cttctgcctg ctgcactttg gagtgatcgg ccccagagg        180 gaagagttcc ccaggggacct ctctctaatc agccctctgg cccaggcagt cagatcatct      240
tctcgaaccc cgagtgacaa gcctgtagcc catgttgtag caaaccctca agctgagggg       300
cagctccagt ggctgaaccg ccgggccaat gccctcctgg ccaatggcgt ggagctgaga       360
gataaccagc tggtggtgcc atcagagggc ctgtacctca tctactccca ggtcctcttc      420
aagggccaag ctgccccctc cacccatgtg ctcctcaccc acaccatcag ccgcatcgcc       480
gtctcctacc agaccaaggt caacctcctc tctgccatca agagccctg ccagagggag       540 accccagagg gggctgaggc caagccctgg tatgagccca tctatctggg aggggtcttc      600
cagctggaga agggtgaccg actcagcgct gagatcaatc ggcccgacta ctcgactttt      660
gccgagtctg gcaggtcta ctttgggatc attgccctg                              699

<210> SEQ ID NO 12
<211> LENGTH: 729
<212> TYPE: DNA
<213> ORGANISM: Artificial sequence
<220> FEATURE:
<223> OTHER INFORMATION: Nucleic acid sequence encoding TNFRGD4C fusion
      polypeptide

<400> SEQUENCE: 12
atgagcactg aaagcatgat ccgggacgtg gagctggccg aggaggcgct ccccaagaag        60 acagggggc cccagggctc caggcggtgc ttgttcctca gcctcttctc cttcctgatc       120
gtggcaggcg ccaccacgct cttctgcctg ctgcactttg gagtgatcgg ccccagagg        180 gaagagttcc ccaggggacct ctctctaatc agccctctgg cccaggcagt cagatcatct      240
tctcgaaccc cgagtgacaa gcctgtagcc catgttgtag caaaccctca agctgagggg       300
cagctccagt ggctgaaccg ccgggccaat gccctcctgg ccaatggcgt ggagctgaga       360
gataaccagc tggtggtgcc atcagagggc ctgtacctca tctactccca ggtcctcttc      420
```

-continued

```
aagggccaag gctgccctc  cacccatgtg ctcctcaccc acaccatcag ccgcatcgcc    480
gtctcctacc agaccaaggt caacctcctc tctgccatca agagccctg  ccagagggag    540 accccagagg gggctgaggc caagccctgg tatgagccca tctatctggg aggggtcttc    600
cagctggaga agggtgaccg actcagcgct gagatcaatc ggcccgacta tctcgacttt    660
gccgagtctg ggcaggtcta ctttgggatc attgccctgt gcgattgccg tggtgattgc    720
ttttgctga                                                            729
```

IMAGING-AIDED GENE THERAPY USING MESENCHYMAL STEM CELLS AS TARGET-DELIVERY VEHICLE

CROSS-REFERENCE TO RELATED APPLICATIONS

This application is the 35 U.S.C. §371 national stage of PCT Application No. PCT/US2013/037315, entitled "IMAGING-AIDED GENE THERAPY USING MESENCHYMAL STEM CELLS AS TARGET-DELIVERY VEHICLE" and filed Apr. 19, 2013, which is hereby incorporated by reference in its entirety, and which claims priority to, and the benefit of, U.S. Provisional Application No. 61/635,422, filed Apr. 19, 2012, which is hereby incorporated by reference in its entirety.

STATEMENT REGARDING FEDERALLY SPONSORED RESEARCH OR DEVELOPMENT

This invention was made with Government support under contract W81XWH-07-1-0374 awarded by the Department of Defense. The Government has certain rights in this invention.

SEQUENCE LISTING

The present disclosure includes a sequence listing incorporated herein by reference in its entirety.

TECHNICAL FIELD

The present disclosure is generally related to the use of genetically modified mesenchymal stem cells to target tumors.

BACKGROUND

At present, cancer is still a leading cause of mortality and morbidity throughout the world. Conventional cancer therapies include surgery, chemotherapy and radiotherapy. Despite healthcare improvements, many tumors remain unresponsive to traditional therapy, and thus investigation for a new modality of treatment has been urgently expected.

Mesenchymal stem cells (MSCs) were first discovered in the bone marrow in 1960s (Friedenstein et al., (1966) *J. Embryol. Exp. Morphol.* 16: 381-390; Friedenstein et al., (1968) *Transplantation* 6: 230-247) and were first considered as stem cells by Caplan and named mesenchymal stem cells in 1991 (Caplan A. I., *J. Orthop. Res.* 9: 641-650). MSCs were also the first type of stem cells utilized in clinical regenerative medicine due to their attractive features such as easy isolation, rapid ex vivo expansion, feasibility of autologous transplantation and their powerful paracrine function (Gregory et al., (2005) *Sci. STKE* 294: pe37). Recently it has been shown that bone marrow-derived stem cells (BMSCs) are able to migrate specifically to tumor cells in vitro using transwell migration assays (Loebinger et al., (2009) *Cancer Res.* 69: 4134-442; Nakamizo et al., (2005) *Cancer Res.* 65: 3307-3318; Menon et al., (2007) *Stem Cells* 25: 520-528; Xin et al., (2007) *Stem Cells* 25: 1618-1626) and in vivo using animal tumor models (Studeny et al., (2002) *Cancer Res.* 62: 3603-3608; Studeny et al., (2004) *J. Natl. Cancer Inst.* 96: 1593-1603; Khakoo et al., (2006) *J. Exp. Med.* 203: 1235-1247; Wang et al., (2009) *Stem Cells* 27(7): 1548-1558) although the specific molecular mechanisms are not understood. This tumor-directed migration and incorporation of MSCs makes them promising cell-based delivery vehicles for cancer therapy. By combining with anticancer genes, utilization of engineered MSCs has inspired an efficient approach for cancer therapy (Loebinger et al., (2009) *Cancer Res.* 69: 4134-442; Xin et al., (2007) *Stem Cells* 25: 1618-1626; Ren et al., (2008) *Stem Cells* 26: 2332-2338; Ren et al., (2008) *Gene Ther.* 15: 1446-1453; Kanehira et al., (2007) *Cancer Gene Ther.* 14: 894-903).

Tumor necrosis factor (TNF, formerly referred to as TNF-alpha (TNFα)) is a cytokine with well-known anticancer properties and is being utilized as an agent for the treatment of patients with locally advanced solid tumors (Tomita et al., (1998) *Anticancer Res.* 18: 3937-3939). However, clinical applications of TNFα for cancer therapy are still limited because TNF has been found to have toxic side effects, such as fever and decreased blood pressure similar to endotoxin-like shock, before therapeutic doses can be reached (Wang et al., (2006) *Protein Expr. Purif.* 45: 60-65). TNF has been applied to treatment of cancer for decades. Study on potential mechanisms underlying the variability in cell sensitivity to TNF-driven cytotoxicity is continuing so as to develop novel methods for enhancing TNF anticancer properties and minimizing side effects. Deleting domains of TNF responsible for causing systemic toxicity is one of several strategies (Gerspach et al., (2009) *Biofactors* 35: 364-372). Making TNF mutants selectively binding to TNFR was previously reported (Ameloot & Brouckaert (2004) *Methods Mol. Med.* 98: 33-46; Novakovic et al., (1997) *Cytokine* 9: 597-604). Other strategies included interfering with the NFkB Pathway (Zwacka et al., (2000) *J. Gene Med.* 2: 334-343; Wang et al., (1999) *Nat. Med.* 5: 412-417), co-administration of inhibitor of Nitric Oxide Synthase (NOS) (de Wilt et at, (2000) *Br. J. Cancer* 83: 1176-1182), changing the administration route of TNF alone or in combination with conventional drugs to enhance the delivery efficiency of TNF or conventional drugs (Bartlett et al., (1998) *Cancer* 83: 1251-1261) and gene therapy that achieves selective intra-tumoral TNF expression by utilizing radiation-induced activation of viral vectors (Weichselbaum et al., (2002) *Lancet Oncol.* 3: 665-671). There remains, therefore, an on-going need for more effective and targeted application of TNF directed against tumor cells and with reduced side-effects seen with generalized administration of TNF to a patient.

SUMMARY

To improve anti-tumor effects and reduce side effects of TNF, the present disclosure provides compositions and methods of use thereof that encompass the use of engineered MSCs as vehicle to deliver secreted TNF-RGD4C for tumor treatment. In addition, to track engineered MSCs during in vivo treatment, dual reporter gene mrfp-ttk was also included in lentiviral vector constructs to monitor the localization and viability of engineered MSCs after administration into mice. One aspect of the present disclosure, therefore, provides embodiments encompassing a genetically modified mesenchymal stem cell that comprises an expression cassette, wherein said cassette can comprise a nucleic acid sequence operably linked to a gene expression promoter and encoding a heterologous fusion polypeptide, the heterologous polypeptide comprising a tissue necrotic factor region and an integrin-binding region.

In embodiments of this aspect of the disclosure, the nucleic acid expression vector can be a lentivirus-based vector.

In embodiments of this aspect of the disclosure, the integrin-binding region can comprise the motif arginine-glycine-aspartate.

In embodiments of this aspect of the disclosure, the integrin-binding region is RGD4C and can have the amino acid sequence according to SEQ ID NO.: 8.

In embodiments of this aspect of the disclosure, the tissue necrotic factor region can be TNFα, an isolated bioactive region of a TNFα, or a conservative derivative thereof.

In some embodiments of this aspect of the disclosure, the tissue necrotic factor region can be a wild-type human TNFα, an isolated bioactive region of said wild-type human TNFα, or a conservative derivative thereof.

In some embodiments of this aspect of the disclosure, the tissue necrotic factor region can have an amino acid sequence having at least 75% sequence similarity to SEQ ID NO.: 9.

In some embodiments of this aspect of the disclosure, the heterologous fusion polypeptide can have the amino acid sequence having at least 75% sequence similarity to SEQ ID NO.: 10.

In embodiments of this aspect of the disclosure, the genetically modified mesenchymal stem cell can further comprise a detectable label.

In embodiments of this aspect of the disclosure, the detectable label is a reporter polypeptide, and wherein the nucleic acid expression vector further comprises a region encoding the reporter polypeptide.

In embodiments of this aspect of the disclosure, the reporter polypeptide is selected from the group consisting of: a Renilla fluorescent protein, a luciferase, a red fluorescent protein, a green fluorescent protein, an enhanced green fluorescent protein.

In embodiments of this aspect of the disclosure, the detectable label is a radioactive label or a label detectable by magnetic resonance imaging or by positron emission tomography.

In embodiments of this aspect of the disclosure, the nucleic acid expression vector has the nucleic acid sequence having at least 75% sequence similarity to SEQ ID NO.: 1.

Another aspect of the present disclosure encompasses embodiments of a recombinant nucleic acid comprising an expression cassette comprising a nucleic acid sequence operably linked to a gene expression promoter and encoding a heterologous fusion polypeptide, said heterologous polypeptide comprising a tissue necrotic factor region and an integrin-binding region.

In embodiments of this aspect of the disclosure, the recombinant nucleic acid can be inserted in a vector, wherein the vector can be a lentivirus vector.

In embodiments of this aspect of the disclosure, the integrin-binding region can comprise the motif arginine-glycine-aspartate.

In embodiments of this aspect of the disclosure, the integrin-binding region can be RGD4C having the amino acid sequence having at least 75% sequence similarity to SEQ ID NO.: 8.

In embodiments of this aspect of the disclosure, the tissue necrotic factor region can be TNFα, an isolated bioactive region of a TNFα, or a conservative derivative thereof.

In embodiments of this aspect of the disclosure, the tissue necrotic factor region can have an amino acid sequence having at least 75% sequence similarity to SEQ ID NO.: 9 and be encoded by a nucleic acid sequence having at least 75% sequence similarity to SEQ ID NO.: 11.

In embodiments of this aspect of the disclosure, the heterologous fusion polypeptide can have the amino acid sequence having at least 75% sequence similarity to SEQ ID NO.: 10 and can be encoded by a nucleic acid sequence having at least 75% sequence similarity to SEQ ID NO.: 12.

In embodiments of this aspect of the disclosure, the recombinant nucleic acid can further encode a detectable label.

In these embodiments of this aspect of the disclosure, the detectable label can be selected from the group consisting of: a Renilla fluorescent protein, a luciferase, a red fluorescent protein, a green fluorescent protein, an enhanced green fluorescent protein.

In some embodiments of this aspect of the disclosure, the recombinant nucleic acid has a nucleic acid sequence having at least 75% sequence similarity to SEQ ID NO.: 1.

Still another aspect of the disclosure encompasses embodiments of a method of the proliferation of a targeted population of tumor cells, the method comprising: (i) obtaining a population of genetically modified mesenchymal stem cells according to the disclosure and substantially free of cells not comprising the nucleic acid expression vector encoding the heterologous polypeptide according to the disclosure; (ii) delivering the population of genetically modified mesenchymal stem cells from step (i) to a population of targeted tumor cells; and (iii) allowing the genetically modified mesenchymal stem cells to express the heterologous polypeptide, thereby modulating the proliferation of the targeted tumor cells.

In embodiments of this aspect of the disclosure, the population of genetically modified mesenchymal stem cells substantially free of cells not comprising the nucleic acid expression vector region encoding a heterologous polypeptide can be obtained by FACS.

In embodiments of this aspect of the disclosure, the population of targeted tumor cells can be a population of cultured tumor cells or a population of tumor cells in a tissue of an animal or human subject.

In embodiments of this aspect of the disclosure, the population of targeted tumor cells can be in a tissue of an animal or human subject located in a breast tissue, a lung tissue, a bone, or bone marrow.

In embodiments of this aspect of the disclosure, the population of genetically modified mesenchymal stem cells can be delivered to a recipient animal or human subject intravenously, intraperitoneally, or subcutaneously, or directly to a tumor.

In embodiments of this aspect of the disclosure, the expression of the heterologous polypeptide can inhibit the proliferation of the targeted tumor cells.

In embodiments of this aspect of the disclosure, the method can further comprise the step of monitoring the distribution of the population of genetically modified mesenchymal stem cells in the recipient animal or human subject.

In embodiments of this aspect of the disclosure, the step of monitoring the distribution of the population of genetically modified mesenchymal stem cells in the recipient animal or human subject can comprise detecting bioluminescence, fluorescence, MRI, or PET scanning.

In embodiments of this aspect of the disclosure, the genetically modified mesenchymal stem cells can comprise a nucleic acid vector having the nucleic acid sequence having at least 75% sequence similarity to SEQ ID NO.: 1.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A is a digital image of a Western blot of wild-type TNF-RGD4C expression.

FIG. 1B is a digital image of a Western blot of ttk expression.

FIG. 1C is a graph illustrating the positive correlation between wild-type TNF-RGD4C and RFP expression level observed based on ELISA and FACS results of transduced 293 FT cells. ($r^2$=0.96).

FIG. 6A illustrates ex vivo lung pictures.

FIG. 6B illustrates lung H&E staining images.

FIG. 8 illustrates the nucleic acid sequence of construct pCDH-MSCV-hTNF-RGD4C-EF1-mrfp-ttk.str (SEQ ID NO.: 1).

FIG. 9 illustrates a pair of primers (SEQ ID NOS.: 2 and 3) used to amplify the NheI-wild-type TNFRGD4C-NotI fragment (SE ID NO.: 6), and a second pair of primers (SEQ ID NO.: 4 and 5) to amplify the pacI-mrfp-ttk-XhoI fragment (SEQ ID NO.: 7).

FIG. 10 illustrates the nucleic acid sequence (SEQ ID NO.: 6) of the template for making NheI-wild-type TNFRGD4C-NotI fragment.

FIG. 11 illustrates the partial nucleic acid sequence (SEQ ID NO.: 7) of the template for making pacI-mrfp-ttk-XhoI fragment.

FIG. 12 illustrates the amino acid sequence (SEQ ID NO.: 9) of the TNF fragment.

FIG. 13 illustrates the amino acid sequence (SEQ ID NO.: 10) of the TNFRGD4C fusion polypeptide.

FIG. 14 illustrates the nucleic acid sequence SEQ ID NO.: 11 encoding the amino acid sequence of the TNF fragment according to SEQ ID NO.: 9.

FIG. 15 illustrates the nucleic acid sequence SEQ ID NO.: 12 encoding the TNFRGD4C fusion polypeptide according to SEQ ID NO.: 10.

Figure 1A:
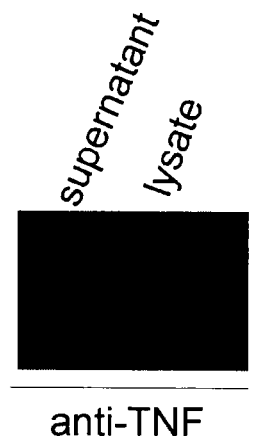
FIGS. 1A-1C illustrate the characterization of dual promoter lentiviral vector pCDH-MSCV-wild-type TNF-RGD4C-EF1-mrfp-ttk of the disclsoure.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

ABBREVIATIONS

MSC, mesenchymal stem cell; TNF, tissue necrosis factor;

DEFINITIONS

In describing and claiming the disclosed subject matter, the following terminology will be used in accordance with the definitions set forth below.

The term "generating an image" as used herein can refer to acquiring a detectable signal generated from a detectably labeled compound and determining the location of the source in a cell or an animal or human tissue. The detectable label suitable for use in the compositions of the disclosure include, but are not limited to, a radioactive element detectable by the particle emissions therefrom, or most advantageously, a luciferase light source such as according to the present disclosure The term "detectably labeled" as used herein refers to a polypeptide or a fragment thereof conjugated to a fluorophore, or that is substituted with some other molecular species that elicits a physical or chemical response that can be observed or detected by the naked eye or by means of instrumentation such as, without limitation, scintillation counters, colorimeters, UV spectrophotometers and the like.

As used herein, a "label" or "tag" refers to a molecule that, when appended by, for example, without limitation, covalent bonding or hybridization, to another molecule, for example, also without limitation, a polynucleotide or polynucleotide fragment, provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence, electrochemiluminescence, raman, colorimetric, hybridization protection assay, and mass spectrometry. Particularly useful in the methods of the present disclosure are reporter polypeptides that are encoded by genetic elements incorporated in the genome of the MSCs. Accordingly, such cells will not dilute out the reporter due to proliferation of the cells—each progeny cell will have the expressed reporter and the intensity of the reporter signal, such as bioluminescence, will have a defined relationship to the number of cells.

The term "reporter" or "reporter polypeptide" as used herein refers to a molecule that may be detected, where the reporter is an adjunct to the cell, nucleic acid or polypeptide under study. The reporter provides a signal such as, but not limited to, a bioluminescence discharge, fluorescent activity, radioactive decay particles, an enzyme activity and the like that may be qualitatively or quantitatively related to the activity or amount of the subject under study. The reporter may be, for example, but is not limited to, an enzyme such as a peroxidase, or a luciferase that in the presence of a bioluminescence initiator emits detectable bioluminescence. Suitable luciferases include, but are not limited to, such as firefly luciferase, Renilla luciferase and the like, or mutants or variants thereof. In particular, the reporter is a polypeptide encoded by a nucleic acid and which may be inserted in the genome of a donor animal, whereby the cells of the subject animal, including stem cells thereof, include the heterologous nucleic acid, and are capable of expressing the reporter polypeptide, and therefore may be specifically detected.

The term "bioluminescence" as used herein refers to a type of chemiluminescence, i.e., emission of light by biological molecules, particularly proteins. The essential condition for bioluminescence is molecular oxygen either bound or free in the presence of an oxygenase. A luciferase, which acts on a substrate, a luciferin, in the presence of molecular oxygen transforms the substrate to an excited state, which upon return to a lower energy level releases the energy in the form of light.

The term "luciferase" as used herein refers to oxygenases that catalyze a light-emitting reaction. For instance, bacterial luciferases catalyze the oxidation of flavin mononucleotide and aliphatic aldehydes, which reaction produces light. Another class of luciferases, found among marine arthropods, catalyzes the oxidation of cypridina luciferin, and another class of luciferases catalyzes the oxidation of coleoptera luciferin. Thus, "luciferase" refers to an enzyme or photoprotein that catalyzes a bioluminescent reaction. The luciferases, such as firefly and Renilla luciferases, are enzymes that act catalytically and are unchanged during the bioluminescence-generating reaction. The luciferase photoproteins, such as the aequorin and obelin photoproteins to which luciferin is non-covalently bound, are changed by release of the luciferin during a bioluminescence-generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known. Reference, for example, to "Renilla luciferase" means an enzyme isolated from a member of the genus Renilla or an equivalent molecule obtained from any other source, such as from another Anthozoa, or that has been prepared synthetically.

"Bioluminescent protein" refers to a protein capable of acting on a bioluminescent initiator molecule substrate to generate or emit bioluminescence.

"Fluorescent acceptor molecule" refers to any molecule that can accept energy emitted as a result of the activity of a bioluminescent donor protein, and re-emit it as light energy.

The term "bioluminescent initiator molecule" as used herein refers to a molecule that can react with a bioluminescent donor protein to generate bioluminescence. The bioluminescence initiator molecule includes, but is not limited to, coelenterazine, analogs thereof, and functional derivatives thereof. Derivatives of coelenterazine include, but are not limited to, coelenterazine 400a, coelenterazine cp, coelenterazine f, coelenterazine fcp, coelenterazine h, coelenterazine hcp, coelenterazine ip, coelenterazine n, coelenterazine O, coelenterazine c, coelenterazine c, coelenterazine i, coelenterazine icp, coelenterazine 2-methyl, benzyl-coelenterazine bisdeoxycoelenterazine, and deep blue coelenterazine (DBC) (described in more detail in U.S. Pat. Nos. 6,020,192; 5,968,750 and 5,874,304).

In general, coelenterazines are known to luminesce when acted upon by a wide variety of bioluminescent proteins, specifically luciferases. Useful, but non-limiting, coelenterazines are disclosed in U.S. patent application Ser. No. 10/053,482, filed Nov. 2, 2001, the disclosure of which is hereby incorporated by reference in its entirety. Coelenterazines are available from Promega Corporation, Madison, Wis. and from Molecular Probes, Inc., Eugene, Oreg. Coelenterazines may also be synthesized as described, for example, in Shimomura et al., (1989) *Biochem. J.* 261: 913-20; Inouye et al., (1997) *Biochem. Biophys. Res. Comm.* 233: 349-53; and Teranishi et al., (1997) *Anal. Biochem.* 249: 37-43.

The terms "fluorescent dye" and "fluorescent label" as used herein include all known fluors, including rhodamine dyes (e.g., tetramethylrhodamine, dibenzorhodamine, see, e.g., U.S. Pat. No. 6,051,719); fluorescein dyes, "BODIPY" dyes, and equivalents thereof.

The term "complemented FL activity" as used herein refers to the luciferase activity generated by the association of two polypeptides derived from a luciferase that, when in proximity to one another interact to provide a detectable luciferase-generated signal. The term may also apply to other species of luciferase including, but not limited to, a human codon-optimized Renilla luciferase.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source such as a bird, or are synthesized. The term "polypeptides" further contemplates polypeptides as defined above that include chemically modified amino acids or amino acids covalently or non-covalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein or polypeptide or a portion thereof.

The term "coding region" as used herein refers to a continuous linear arrangement of nucleotides that may be translated into a protein. A full-length coding region is translated into a full-length protein, that is, a complete protein as would be translated in its natural state absent any post-translational modifications. A full-length coding region may also include any leader protein sequence or any other region of the protein that may be excised naturally from the translated protein.

The terms "percent sequence identity" or "percent sequence similarity" as used herein refer to the degree of sequence identity between two nucleic acid sequences or two amino acid sequences as determined using the algorithm of Karlin & Attschul (1990) *Proc. Natl. Acad. Sci.* 87: 2264-2268, modified as in Karlin & Attschul (1993) *Proc. Natl. Acad. Sci.* 90: 5873-5877. Such an algorithm is incorporated into the NBLAST and XBLAST programs of Attschul et al., (1990) *T. Mol. Biol. Q*15: 403-410. BLAST nucleotide searches are performed with the NBLAST program, score=100, word length=12, to obtain nucleotide sequences homologous to a nucleic acid molecule of the invention. BLAST protein searches are performed with the XBLAST program, score=50, word length=3, to obtain amino acid sequences homologous to a reference polypeptide. To obtain gapped alignments for comparison purposes, Gapped BLAST is utilized as described in Attschul et al. (1997) *Nuc. Acids Res.* 25: 3389-3402. When utilizing BLAST and Gapped BLAST programs, the default parameters of the respective programs (e.g., XBLAST and NBLAST) are used.

The term "nucleic acid vector" as used herein refers to a natural or synthetic single- or double-stranded plasmid or viral nucleic acid molecule that can be transfected or transformed into cells and replicated independently of, or within, the host cell genome. A circular double-stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "isolated" as used herein may refer to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source. The term "isolated" as used herein may also refer to a cell or population of cells removed from its/their natural environment such as a donor animal or tissue thereof, or removed from recognizably differing cells isolated from a subject mammal or tissue thereof.

The term "tissue" as used herein refers to a group or collection of similar cells and their intercellular matrix that act together in the performance of a particular function. The primary tissues are epithelial, connective (including blood), skeletal, muscular, glandular and nervous.

The term "lentivirus" as used herein refers to a genus of retroviruses that can infect dividing and non-dividing cells. Several examples of lentiviruses include HIV (human immunodeficiency virus, including HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus, which causes autoimmune hemolytic anemia and encephalopathy in horses; feline immunodeficiency virus (Fly), which causes immune deficiency in cats; bovine immune deficiency virus (BIV), which causes lymphadenopathy, lymphocytosis, and possibly central nervous system infection in cattle; and simian immunodeficiency virus (Sly), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. (See, for example, "RNA Viruses: A Practical Approach," Alan J. Cann, Ed., Oxford University Press, (2000); Narayan & Clements (1989) *Gen. Virology* 70: 1617-1639; Fields at al., "Fundamental Virology," Raven Press (1990); Miyoshi et al., (1998) *J. Virol.* 72: 8150-8157; U.S. Pat. No. 6,013,516, all of which are incorporated herein by reference in their entireties.)

The term "vector" as used herein refers to a vehicle into which a genetic element encoding a polypeptide may be operably inserted so as to bring about the expression of that polypeptide. A vector may be used to transform, transduce or transfect a subject mammal cell so as to bring about expression of the genetic element it carries within the subject mammal cell. Examples of vectors include plasmids, cosmids, bacmids, bacteriophages such as lambda phage or M13 phage, and animal viruses such as lentivirus, adenovirus, adeno-associated virus (AAV), cytomegalovirus (CMV), herpes simplex virus (HSV), papillomavirus, retrovirus, and simian virus 40 (SV40). A vector utilized as part of an expression system may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. The viral particle may include one or more proteins that help facilitate assembly of the viral particle, transduction of the subject mammal cell, and transport of the vector polynucleotide sequence within the subject mammal cell, among other functions. The term "lentiviral vector" as used herein refers to a lentiviral vector designed to operably insert an exogenous polynucleotide sequence into a subject mammal genome.

The term "expression vector" as used herein refers to a nucleic acid vector that may further include at least one regulatory sequence operably linked to a nucleotide sequence coding for a polypeptide or a protein. Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as Sambrook et al. eds., "Molecular Cloning: A Laboratory Manual," 2nd ed., Cold Spring Harbor Press (1989) may be consulted to design suitable expression vectors, promoters, and other expression control elements. It should be recognized, however, that the choice of a suitable expression vector depends upon multiple factors including the choice of the host cell to be transformed and/or the type of protein to be expressed.

The term "expression cassette" as used herein refers to one or more nucleotide sequences operably linked to a promoter region that can be transcribed to provide a single mRNA transcript that may then be translated to at least one polypeptide.

The terms "transformation" and "transfection" as used herein refer to the process of inserting a nucleic acid into a host. Many techniques to facilitate transformation or transfection of a nucleic acid into a prokaryotic or eukaryotic organism are well known to those skilled in the art. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules.

The term "genetically modified cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, a single prokaryotic cell, or a mammalian cell. The recombinant cell can harbor a vector that is extragenomic. An extragenomic nucleic acid vector does not insert into the cell's genome. A recombinant cell can further harbor a vector or a portion thereof that is intragenomic. The term intragenomic defines a nucleic acid construct incorporated within the recombinant cell's genome.

The term "conservatively modified variation," as used herein in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid.

Conservative amino acid substitutions providing functionally similar amino acids are well known in the art, including the following six groups, each of which contains amino acids that are considered conservative substitutes for each another: 1) Alanine (Ala, A), Serine (Ser, S), Threo nine (Thr, T); 2) Aspartic acid (Asp, D), Glutamic acid (Glu, E); 3) Asparagine (Asn, N), Glutamine (Gln, Q); 4) Arginine (Arg, R), Lysine (Lys, K); 5) Isoleucine (Ile, I), Leucine (Leu, L), Methionine (Met, M), Valine (Val, V); and 6) Phenylalanine (Phe, F), Tyrosine (Tyr, Y), Tryptophan (Trp, V).

Two or more amino acid sequences or two or more nucleotide sequences are considered to be "substantially identical" or "substantially similar" if the amino acid sequences or the nucleotide sequences share at least 75% sequence identity with each other, or with a reference sequence over a given comparison window. Thus, substantially similar sequences include those having, for example, at least 75% sequence identity, at least 85% sequence identity, at least 90% sequence identity, at least 95% sequence identity, or at least 99% sequence identity.

The term "cancer," as used herein shall be given its ordinary meaning and is a general term for diseases in which abnormal cells divide without control. Cancer cells can invade nearby tissues and can spread through the bloodstream and lymphatic system to other parts of the body.

There are several main types of cancer. For example, carcinoma is cancer that begins in the skin or in tissues that line or cover internal organs. Sarcoma is cancer that begins in bone, cartilage, fat, muscle, blood vessels, or other connective or supportive tissue. Leukemia is a cancer that starts in blood-forming tissue such as the bone marrow and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, and cervical cancer.

The term "DNA amplification" as used herein refers to any process that increases the number of copies of a specific DNA sequence by enzymatically amplifying the nucleic acid sequence. A variety of processes are known. One of the most commonly used is the polymerase chain reaction (PCR), which is defined and described in later sections below. The PCR process of Mullis is described in U.S. Pat. Nos. 4,683,195 and 4,683,202. PCR involves the use of a thermostable DNA polymerase, known sequences as primers, and heating cycles, which separate the replicating deoxyribonucleic acid (DNA) strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with termini corresponding to the ends of the specific primers employed.

The term "fragment" of a molecule such as a protein or nucleic acid as used herein refers to any portion of the amino acid or nucleotide genetic sequence.

The term "flow cytometer" as used herein refers to any device that will irradiate a particle suspended in a fluid medium with light at a first wavelength, and is capable of detecting a light at the same or a different wavelength, wherein the detected light indicates the presence of a cell or an indicator thereon. The "flow cytometer" may be coupled to a cell sorter that is capable of isolating the particle or cell from other particles or cells not emitting the second light (FACS).

The term "polymerase chain reaction" or "PCR" as used herein refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569, 627; 6,562,298; 6,556,940; 6,569,672; 6,569,627; 6,562, 298; 6,556,940; 6,489,112; 6,482,615; 6,472,156; 6,413, 766; 6,387,621; 6,300,124; 6,270,723; 6,245,514; 6,232, 079; 6,228,634; 6,218,193; 6,210,882; 6,197,520; 6,174, 670; 6,132,996; 6,126,899; 6,124,138; 6,074,868; 6,036, 923; 5,985,651; 5,958,763; 5,942,432; 5,935,522; 5,897, 842; 5,882,918; 5,840,573; 5,795,784; 5,795,547; 5,785, 926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

The terms "therapeutic agent" or "chemotherapeutic agent" as used herein refers to a compound or a derivative thereof that can interact with a cancer cell, thereby reducing the proliferative status of the cell and/or killing the cell.

The terms "therapeutically effective amount" and "therapeutic dose" as used herein refer to that amount of the compound being administered which will relieve to some extent one or more of the symptoms of a disease, a condition, or a disorder being treated. In reference to cancer or pathologies related to unregulated cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer or angiogenesis.

The terms "subject" and "patient" as used herein refer to humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals, particularly pets such as dogs and cats. For diagnostic or research applications, a wide variety of mammals will be suitable subjects, including rodents (e.g., mice, rats, hamsters), rabbits, primates, and swine such as inbred pigs and the like. In some embodiments, a system includes a sample and a subject. The term "living host" refers to host or organisms noted above that are alive and are not dead. The term "living host" refers to the entire host or organism and not just a part excised (e.g., a liver or other organ) from the living host.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide, or a portion or fragment thereof.

The term "promoter" as used herein refers to the DNA sequence that determines the site of transcription initiation from an RNA polymerase. A "promoter-proximal element" may be a regulatory sequence within about 200 base pairs of the transcription start site.

The term "nucleic acid vector" as used herein refers to a natural or synthetic single- or double-stranded plasmid or viral nucleic acid molecule that can be transfected or transformed into cells and replicate independently of, or within, the host cell genome. A circular double-stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The terms "operably" or "operatively linked" as used herein refer to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous," as they relate to nucleic acid sequences such as coding sequences and control sequences, denote sequences that are not normally associated with a region of a recombinant construct or with a particular chromosomal locus and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct tip could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40, the Rous sarcoma virus (RSV), and CMV promoters, are active in a wide array of cell types and are termed "constitutive" or "ubiquitous." The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

The termination region which is employed primarily will be one of convenience, since termination regions appear to be relatively interchangeable. The termination region may be native to the intended nucleic acid sequence of interest, or may be derived from another source.

The term "vector" as used herein refers to a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed and translation initiation and termination sites.

A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

The terms "transformation," "transduction," and "transfection" all denote the introduction of a polynucleotide into a recipient cell or cells.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

DESCRIPTION

To improve the anti-tumor effect and reduce side effects of TNF, the present disclosure provides genetically modified mesenchymal stem cells that advantageously deliver secreted TNF-RGD4C for targeted tumor treatment, and methods of use thereof. Most advantageously, to track the engineered MSCs during in vivo treatment, a dual reporter gene such as that encoding mrfp-ttk was also included in the lentiviral vector constructs to provide a detectable label that remains associated with the genetically modified MSCs of the disclosure. This allows the monitoring of the localization and viability of engineered MSCs after administration into a living subject and provides a means of monitoring the progress of an anti-tumor treatment in the recipient subject.

To establish the efficacy of the anti-tumor activity of the compositions and methods of the disclosure, an exemplary mammalian animal experimental model was used, namely a murine lung metastasis model of breast cancer cells. It is contemplated, however, that the methods and compositions of the disclosure may be readily adapted for use in reducing the proliferation or survivability of tumors originating from tissues other than just breast tissue and in recipient subjects such as, but not limited to, humans. Accordingly, the compositions and methods of the disclosure are suitable for both human medical applications and in the veterinary field for the treatment of non-human cancers.

Systemic toxicity of tumor necrosis factor (TNF) is a major concern for its application in anticancer therapy and new treatment approaches are urgently needed. Studies have suggested that bone marrow-derived mesenchymal stem cells (MSCs) home to and incorporate within tumor tissue. The present disclosure, therefore, provides isolated and cultured MSCs genetically engineered to produce and deliver a therapeutic fusion protein, most advantageously the fusion TNF-RGD4C having the amino acid sequence according to SEQ ID NO.: 10 or a conservative variant thereof, that can advantageously home to and kill cancer cells, for example in, but not limited to, a lung metastatic cancer model. Accordingly, for example, isolated murine MSCs were transduced with a dual-promoter lentiviral vector containing a cDNA encoding TNF-RGD4C and an mrfp-ttk reporter gene. After incubation with secreted TNF-RGD4C from the MSCs for 48 h, the relative proliferation rate of fLuc-4T1, a murine breast cancer cell line stably expressing firefly luciferase, was reduced up to 33.4%. Also, co-culturing of fLuc-4T1 with engineered MSCs for different periods of time significantly inhibited the growth of fLuc-4T1 and this inhibitory effect was strengthened over the time period.

In vivo tumor treatment confirmed that the engineered MSCs according to the disclosure were able to reduce tumor growth as assessed by bioluminescence imaging. Thus, for example, the relative tumor growth of three groups of animals (transfected MSCs, no treatment, and control MSCs) was 5.5 versus 18.2 versus 27.3 at day 28 (P<0.05). No significant differences of body weight between three groups were observed, indicating the side effects of TNF-RGD4C were effectively minimized. In vivo findings were further corroborated by the ex vivo histological analysis. The data, therefore, support the use of the dual-functional lentiviral gene expression system to deliver TNF-RGD4C for tumor treatment and mrfp-ttk reporter gene that enables in vivo tracking of MSCs during treatment. This approach not only reduces the systemic side effects of TNF but also allows real-time monitoring of MSCs noninvasively.

In the compositions of the present disclosure, MSCs were used as cell-based delivery vehicles that can constitutively express from a nucleic acid expression cassette a therapeutic recombinant gene product such as TNF-RGD4C. Bone marrow-derived MSCs have a tumor-homing property and can eventually become part of stoma cells in a tumor, which helps provide a local accumulation of secreted therapeutic protein. Particularly, in terms of TNF-related cancer therapy, this strategy has several advantages. First, high-dose systemic administration of TNF is well-known to cause side effects such as hypotension that can progress to a shock-like syndrome, with possible fatal consequences to the patient. Furthermore, at a maximum tolerated dose (150-300 ug/m$^2$), TNF systemic administration is not associated with significant anti-tumor activity (Restifo & Rosenberg, *Cancer Principles and Practice of Oncology*, 8th ed., (2000) Philadelphia, Pa.: Lippincott Williams & Wilkins).

In contrast to the effects from using systemically delivered TNF, recipients of the engineered MSCs according to the disclosure exhibit little or no significant body weight loss between when treated with no MSCs or with MSCs expressing TNF-RGD4C. This result indicated that the side-effects of TNF can be significantly reduced due to local distribution of TNF by means of this cell-based delivery system of the disclosure.

It was previously reported that low-dose TNF can actually promote the proliferation of some malignant cell lines and favor cancer development (Wu et al., (1993) *Cancer Res.* 53: 1939-1944; Liu et al., (2000) *J. Biol. Chem.* 275: 21086-21093; Suganuma et al., (1999) *Cancer Res.* 59: 4516-4518). In contrast, this was not observed with the MSCs according to the disclosure that express therapeutic amounts of TNF-RGD4C protein since the expressed protein accumulated around tumor site and reached high localized concentrations (TNF is hard to diffuse). This localized accumulation of TNF results from the fusion of RGD4C to the C-terminal of TNF. The secreted fusion protein then has an enhanced capacity to target tumor vasculature where integrin $\alpha_v\beta_3$ is expressed on the new blood vessels, boosting the tumor growth inhibition effect.

Using MSCs as a cell-based delivery vehicle raised the issue of whether the MSCs themselves can have an adverse effect on tumor control. Accordingly, one group of mice received wild-type MSCs with the same dose and timing as was used in experiments that had shown the regression of tumors with cells expressing the TNF-RGD4C fusion protein. Compared to the group of animals bearing a tumor but not receiving any treatment, the tumor growth in animals receiving MSCs alone was faster, as is shown in FIG. 5, demonstrating that wild-type MSCs alone can favor tumor development and in agreement with observations reported previously (Burns et al., (2005) *Cancer Res.* 65: 3126-3135; Matushansky et al., (2007) *J. Clin. Invest.* 117: 3248-3257). While not wishing to be bound by any one theory, MSCs may have self-renewal ability and high frequency spontaneous transformation properties. However, it has also been demonstrated that MSCs can inhibit tumor growth in vivo and decrease the proliferation/invasion of the hepatoma cells (Qiao et al., (2008) *Cell Res.* 18: 500-507).

Accordingly, the present disclosure provides a genetically modified mesenchymal stem cell, or progeny thereof, that expresses a heterologous recombinant nucleic acid encoding a fusion protein comprising an integrin binding domain and TNFα, or a bioactive variant thereof.

Also provided are constructs that include the subject polynucleotides inserted into a vector, where such constructs may be used for a number of different applications, including propagation, protein production, and the like. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the disclosure is expressed in any convenient expression system, including, for example, bacterial, yeast, insect, amphibian and mammalian systems. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region and a transcriptional and translational termination region. These control regions may be native to the subject species from which the subject nucleic acid is obtained or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared including a transcription initiation region, the gene or fragment thereof, and a transcriptional termination region. Of particular interest is the use of sequences that allow for the expression of functional domains of the encoded polypeptide, usually at least about 8 amino acids in length, at least about 15 amino acids in length, to about 25 amino acids, and up to the complete open reading frame of the gene. After introduction of the DNA, the cells containing the construct may be selected by means of a selectable marker, the cells expanded, and then used for expression.

Particularly advantageous, but not limiting, for use in the genetically modified mesenchymal stem cells of the present disclosure is the human wild-type TNFα (a recombinant mutant human TNFα was ineffective in providing a secreted TNFα). The integrin-binding domain, such as but not limited to an RGD domain, enables the recombinant fusion protein to bind to integrins of the cell walls of the newly formed vasculature of the targeted tumor mass, thereby concentrating the TNF in the vicinity of the tumor cells and reducing undesirable side-effects on the patient that are typically seen if TNF is administered systemically. The genetically modified MSCs as disclosed herein, therefore, advantageously overcome the adverse effects of systemic TNF administered to a patient and do not display tumor cell growth promoting properties of unmodified (wild-type) MSCs.

The disclosure further provides that the genetically modified MSCs can express a reporter gene that provides a detectable label that can allow an operator to determine the position and extent of the localization of the recombinant cells in a recipient host animal. Not only does such expression allow the operator to assess the extent of delivery of the TNF-producing MSCs to the targeted tumor location, but it can also provide information that allows adjustment of the dose of administered cells to increase or decrease the extent of the treatment. Accordingly, the heterologous recombinant nucleic acid delivered to the MSCs can further comprise a region encoding a polypeptide reporter (such as, but not limited to, a red luminescent protein) that can provide a signal detectable by such as bioluminescent imaging, PET scanning, and the like. It is contemplated that any similar protein reporter, including a green fluorescent protein, an enhanced green fluorescent protein, and the like, is suitable for use in the compositions and methods of the present disclosure.

The genetically modified cells of the present disclosure may be generated by obtaining an isolated population of mesenchymal stem cells from the marrow of a suitable donor and culturing them to expand their number. The isolated population of MSCs may then be transformed with a nucleic acid vector comprising a first region encoding an TNFα-RGD4C fusion polypeptide under the expression control of a first constitutive promoter, and, optionally, a second region encoding a reporter polypeptide under the control of a second expression control region.

Vectors suitable for the delivery of the heterologous nucleic acids herein disclosed to an isolated MSC are well-known in the art, but lentivirus vectors are especially useful. Such vectors may be delivered to the recipient MSCs by techniques well known to those in the art, such as, but not limited to, the method of Example 3 below.

To ensure that only transformed cells are preferentially delivered to an animal or human subject, the cells, after the transformation step, are sorted by FACS analysis to isolate a population of cells substantially free of cells not expressing the reporter polypeptide and hence also not expressing the TNFα-RGD4C fusion protein. Accordingly, the population of cells that is ultimately delivered to the recipient subject will have a significantly reduced likelihood of including MSCs cells that could promote tumor cell proliferation.

It is further contemplated that the genetically modified cells of the present disclosure can be useful in delivering the fusion protein to any tumor targeted by the tropism property of the MSCs, including, but not limited to, tumors of the breast, lung, liver, and kidney.

One aspect of the present disclosure, therefore, provides embodiments encompassing a genetically modified mesenchymal stem cell that comprises an expression cassette comprising a nucleic acid sequence operably linked to a gene expression promoter and encoding a heterologous fusion polypeptide, the heterologous polypeptide comprising a tissue necrotic factor region and an integrin-binding region.

In embodiments of this aspect of the disclosure, the nucleic acid expression vector can be a lentivirus-based vector.

In embodiments of this aspect of the disclosure, the integrin-binding region can comprise the motif arginine-glycine-aspartate.

In embodiments of this aspect of the disclosure, the integrin-binding region is RGD4C and can have the amino acid sequence according to SEQ ID NO.: 8.

In embodiments of this aspect of the disclosure, the tissue necrotic factor region can be TNFα, an isolated bioactive region of a TNFα, or a conservative derivative thereof.

In some embodiments of this aspect of the disclosure, the tissue necrotic factor region can be a wild-type human TNFα, an isolated bioactive region of said wild-type human TNFα, or a conservative derivative thereof.

In some embodiments of this aspect of the disclosure, the tissue necrotic factor region can have an amino acid sequence having at least 75% sequence similarity to SEQ ID NO.: 9.

In some embodiments of this aspect of the disclosure, the heterologous fusion polypeptide can have the amino acid sequence having at least 75% sequence similarity to SEQ ID NO.: 10.

In embodiments of this aspect of the disclosure, the genetically modified mesenchymal stem cell can further comprise a detectable label.

In embodiments of this aspect of the disclosure, the detectable label is a reporter polypeptide, and the nucleic acid expression vector can further comprise a region encoding the reporter polypeptide.

In embodiments of this aspect of the disclosure, the reporter polypeptide is selected from the group consisting of: a Renilla fluorescent protein, a luciferase, a red fluorescent protein, a green fluorescent protein, an enhanced green fluorescent protein.

In embodiments of this aspect of the disclosure, the detectable label is a radioactive label or a label detectable by magnetic resonance imaging or by positron emission tomography.

In embodiments of this aspect of the disclosure, the nucleic acid expression vector has the nucleic acid sequence having at least 75% sequence similarity to SEQ ID NO.: 1.

Another aspect of the present disclosure encompasses embodiments of a recombinant nucleic acid comprising an expression cassette comprising a nucleic acid sequence operably linked to a gene expression promoter and encoding a heterologous fusion polypeptide, said heterologous polypeptide comprising a tissue necrotic factor region and an integrin-binding region.

In embodiments of this aspect of the disclosure, the recombinant nucleic acid can be inserted in a vector, wherein the vector can be a lentivirus vector.

In embodiments of this aspect of the disclosure, the integrin-binding region can comprise the motif arginine-glycine-aspartate.

In embodiments of this aspect of the disclosure, the integrin-binding region can be RGD4C having the amino acid sequence having at least 75% sequence similarity to SEQ ID NO.: 8.

In embodiments of this aspect of the disclosure, the tissue necrotic factor region can be TNFα, an isolated bioactive region of a TNFα, or a conservative derivative thereof.

In embodiments of this aspect of the disclosure, the tissue necrotic factor region can have an amino acid sequence having at least 75% sequence similarity to SEQ ID NO.: 9 and be encoded by a nucleic acid sequence having at least 75% sequence similarity to SEQ ID NO.: 11.

In embodiments of this aspect of the disclosure, the heterologous fusion polypeptide can have the amino acid sequence having at least 75% sequence similarity to SEQ ID NO.: 10 and can be encoded by a nucleic acid sequence having at least 75% sequence similarity to SEQ ID NO.: 12.

In embodiments of this aspect of the disclosure, the recombinant nucleic acid can further encode a detectable label.

In these embodiments of this aspect of the disclosure, the detectable label can be selected from the group consisting of: a Renilla fluorescent protein, a luciferase, a red fluorescent protein, a green fluorescent protein, an enhanced green fluorescent protein.

In some embodiments of this aspect of the disclosure, the recombinant nucleic acid has a nucleic acid sequence having at least 75% sequence similarity to SEQ ID NO.: 1.

Still another aspect of the disclosure encompasses embodiments of a method of modulating the proliferation of a targeted population of tumor cells, the method comprising: (i) obtaining a population of genetically modified mesenchymal stem cells according to the disclosure and substantially free of cells not comprising the nucleic acid expression vector encoding the heterologous polypeptide according to the disclosure; (ii) delivering the population of genetically modified mesenchymal stem cells from step (i) to a population of targeted tumor cells; and (iii) allowing the genetically modified mesenchymal stem cells to express the heterologous polypeptide, thereby modulating the proliferation of the targeted tumor cells.

In embodiments of this aspect of the disclosure, the population of genetically modified mesenchymal stem cells substantially free of cells not comprising the nucleic acid expression vector region encoding a heterologous polypeptide can be obtained by FACS.

In embodiments of this aspect of the disclosure, the population of targeted tumor cells can be a population of cultured tumor cells or a population of tumor cells in a tissue of an animal or human subject.

In embodiments of this aspect of the disclosure, the population of targeted tumor cells can be in a tissue of an animal or human subject located in a breast tissue, a lung tissue, a bone, or bone marrow.

In embodiments of this aspect of the disclosure, the population of genetically modified mesenchymal stem cells can be delivered to a recipient animal or human subject intravenously, intraperitoneally, or subcutaneously, or directly to a tumor.

In embodiments of this aspect of the disclosure, the expression of the heterologous polypeptide can inhibit the proliferation of the targeted tumor cells.

In embodiments of this aspect of the disclosure, the method can further comprise the step of monitoring the distribution of the population of genetically modified mesenchymal stem cells in the recipient animal or human subject.

In embodiments of this aspect of the disclosure, the step of monitoring the distribution of the population of genetically modified mesenchymal stem cells in the recipient animal or human subject can comprise detecting bioluminescence, fluorescence, MRI, or PET scanning.

In embodiments of this aspect of the disclosure, the genetically modified mesenchymal stem cells can comprise a nucleic acid vector having the nucleic acid sequence having at least 75% sequence similarity to SEQ ID NO.: 1.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Mouse Bone Marrow MSCs Isolation

Female Bab/c mice at 6-8 weeks old were sacrificed by cervical dislocation. Mice femurs and tibiae were carefully removed and cleaned from adherent soft tissue. The tip of each bone was removed with a rongeur, and the marrow was harvested by inserting a syringe needle (27-gauge) into one end of the bone and flushing with maintenance medium (Dulbecco's modified Eagle's medium [DMEM] with L-glutamine supplemented with 10% fetal bovine serum [FBS] and 25 µg/ml gentamicin) on poly-L-lysine (PLL)-coated flasks. The bone marrow cells were filtered through a 70-Im nylon mesh filter (BD Falcon; BD Biosciences, San Diego). Cells were plated into a 6-well cell culture plate and cultures were kept at 37° C. in a cell culture incubator with humidified atmosphere containing 95% air and 5% $CO_2$. The adhered cells were split when they reached 80%-90% confluence. The MSCs surface marker expression profile was tested and confirmed by FACS.

Example 2

Cell Lines

The human glioblastoma cell line U87-MG was purchased from American Type Culture Collection and was maintained in Minimum Essential Medium (MEM, cat#11095, Invitrogen) supplemented with 10% fetal bovine serum (FBS), non-essential amino acid (NEAA) and sodium pyruvate at 37° C. with 5% $CO_2$. The cells were used when they reached 70% to 85% confluence. The stably-expressing firefly luciferase (fLuc) murine breast cancer cell line fLuc-4T1 was generated as described previously in Cao et al., (2008) Clin. Cancer Res. 14: 6137-6145, incorporated herein by reference in its entirety.

Example 3

TNF-RGD4C Lentivirus Construction and Transfection of MSCs

Figure 7:
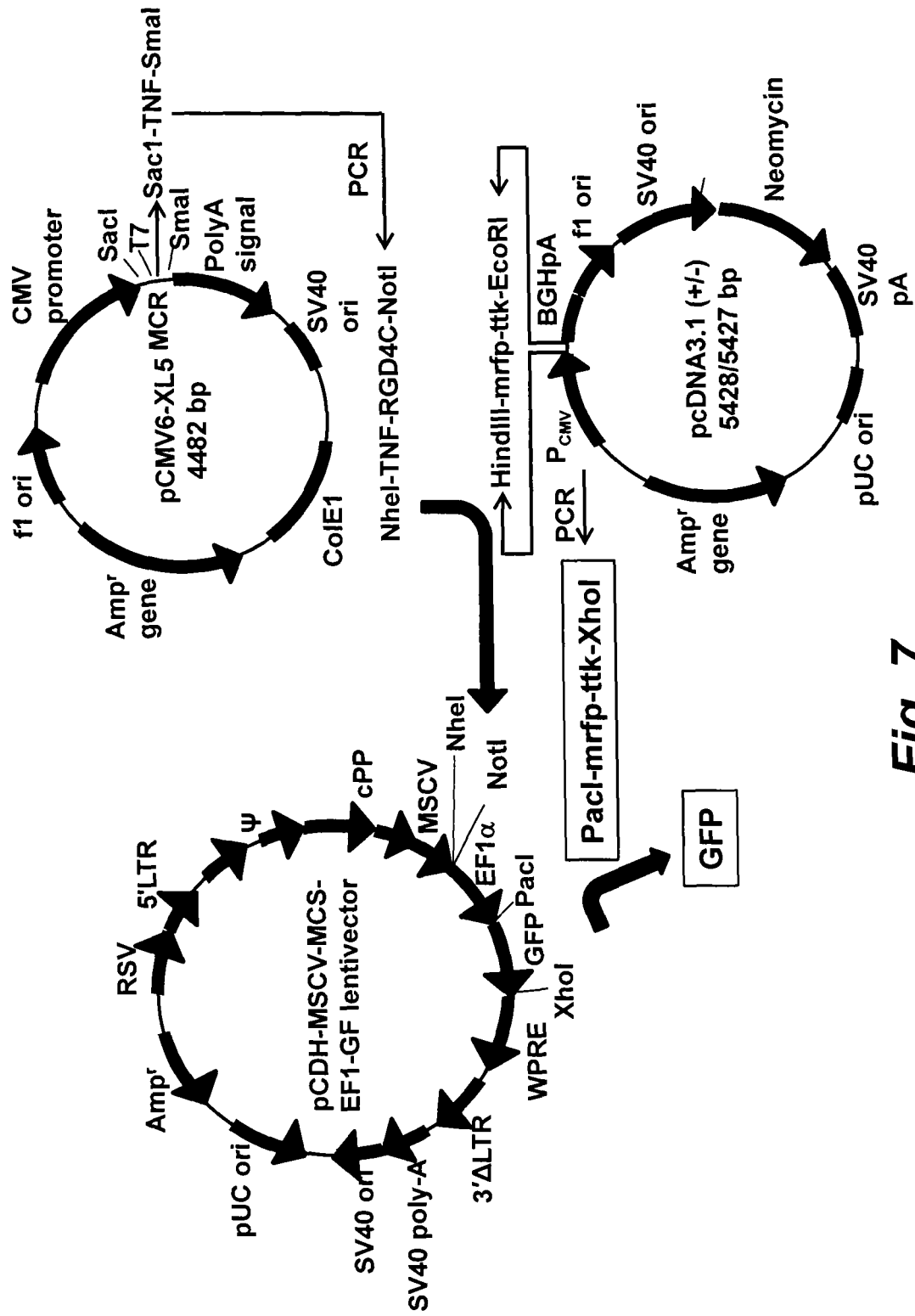
FIG. 7 schematically illustrates the cloning strategy to make the lentiviral vector pCDH-MSCV-rmhTNF-EF1-mrfp-ttk having the nucleic acid sequence SEQ ID NO.: 1.

A lentiviral plasmid (pCDH-MSCV-MCS-EF1-copGFP, System Biosciences (SBI), Mountain view, CA) was used as the backbone for the incorporation of fused wild type (wt) TNF-RGD4C DNA and reporter gene mrfp-ttk. The production and characterization of the wild-type human TNF and RGD4C fusion polypeptide were described in Wang et al., (2008) Mol. Cancer Therap. 7: 1044-1053, incorporated herein by reference in its entirety. As shown in FIG. 7, first, the restriction site of PacI was inserted upstream of the GFP sequence by using GeneTailor Site-Directed Mutagenesis system (Invitrogen). Also, a XhoI site was added at the 3' end of the GFP sequence using the same strategy. The fragment of mrfp-ttk was amplified from the vector of pcDNA3.1-hrl-mrfp-ttk with PacI added to the 5' end and XhoI added to the 3' end. Both the PCR product (SEQ ID NO.: 7) and the modified pCDH-MSCV-MCS-EF1-GFP were digested with PacI and XhoI and the fragment of mrfp-ttk inserted downstream of the EF1 promoter to replace the GFP sequence. The TNF-RGD4C fragment was synthesized by PCR using pCMV6-XL5 containing a full-length human TNF cDNA (Origene) and the restriction sites of NheI and NotI were added respectively to the 5' and 3' end (to give SEQ ID NO.: 6) by PCR. Both the PCR product and the modified vector of pCDH-MSCV-MCS-EF1-GFP were digested with NheI and NotI and ligated by T4 ligase to make lentiviral vector pCDH-MSCV-hTNF-RGD4C-EF1-mrfp-ttk having the nucleic acid sequence SEQ ID NO.: 1. The lentivirus was produced and concentrated following instructions of the lentiviral gene expression system handbook (SBI) incorporated herein by reference in its entirety. Mice bone marrow MSCs were transduced with a multiplicity of infection of 10 virus particles for each cell and 5 µg/mL polybrene (Sigma-Aldrich). Expression of TNF and ttk was verified by Western blot. Concentration of secreted TNF-RGD4C was measured by ELISA (Thermo Scientific) as per the manufacturer's instructions. Sequences (SEQ ID NOs.: 1-7) for the nucleic acids used in the generation of the above constructs are presented in FIGS. 8-11.

Example 4

Western Blot

293FT cells were transduced with pseudoviral particles for 48 h. Supernatant was collected and cells were rinsed three times with 1×PBS and then lysed with RIPA cell lysis buffer. The concentration of cell total protein was measured by microBCA protein assay kit (Pierce Biotechnology, Inc., Rockford, Ill., USA). After sodium dodecyl sulfate-polyacrylamide gel electrophoresis separation of 100 µg of total protein, it was transferred to a polyvinylidene fluoride (PVDF) membrane (Invitrogen Corp.; Carlsbad, Calif., USA) and incubated at room temperature with 5% nonfat milk blocking buffer. The blots were then incubated overnight at 4° C. with primary antibody, followed by incubation at room temperature for 1 h with horseradish peroxidase (HRP)-conjugated secondary antibody. The bands were visualized using an enhanced chemiluminescent Western blotting detection system (GE healthcare).

For TK detection, goat anti-HSV-1 thymidine kinase primary antibody (Santa Cruz Biotechnology) and HRP-conjugated anti-goat secondary were used. Rabbit anti-TNF primary antibody (Abcam) and HRP-conjugated anti-rabbit secondary antibody (GE Healthcare) were used for TNF detection.

Example 5

Tumor Cell Proliferation Inhibition of Secreted TNF-RGD4C Protein

The concentration of TNF-RGD4C protein in supernatant from MSCs was measured by ELISA assay (Thermo Scientific). $2 \times 10^4$ fLuc-4T1 cells were seeded on each well of a 96-well plate. Supernatant containing a known concentration of TNF-RGD4C was added into each well the next day and incubated for 48 h. The wells without the addition of TNF-RGD4C were set as control. Bioluminescence imaging (BLI) was conducted using the IVIS200 system (Caliper Life Sciences). The relative tumor cell proliferation rate was calculated by dividing the total photon flux of the BLI signal from each well by the signal from the control well.

Example 6

Co-Culturing Experiments $2 \times 10^4$ Murine MSCs permanently transduced with TNF-RGD4C were plated with the same amount of fLuc-4T1 in each well of a 48-well plate. The wells with non-transduced MSCs and fLuc-4T1 were set as controls. BLI was conducted at day 2, day 4, and day 6 using the IVIS200 system (Caliper Life Sciences). The relative tumor cell proliferation rate was calculated by dividing the total photon flux of the BLI signal from each well by the signal from the control well.

Example 7

Cell Adhesion Assay

A 96-well plate was pre-coated with anti-TNF antibody overnight at 4° C. and then rinsed three times with 1×PBS. Cell culture medium containing secreted TNF-RGD4C was added to a 96-well plate and incubated overnight after quantification of TNF concentration by ELISA assay. After rinsing with PBS three times, 5×10⁴ integrin αvβ3-positive U87MG human glioblastoma cells were added to each well and incubated for 2 h at 37° C. Each well was washed with PBS three times to remove unattached U87MG cells. U87MG cells were stained with 0.2% (w/v) crystal violet, 10% (v/v) ethanol at room temperature for 10 min. and then solubilized with a 1:1 ratio of PBS:absolute ethanol for ten min. with agitation. The $A_{600}$ was measured using a microplate reader.

Example 8

Experimental Lung Metastasis Model and Treatment Protocol

The fLuc-4T1 breast cancer experimental lung metastasis model was established by intravenous injection of 2×10⁴ fLuc-4T1 cells in 50 μl of PBS into 6-wk-old female BALB/C mice (Harlan). Animals were divided into three groups (no treatment, control MSCs, and transfected MSCs) with 6 mice in each group. The day of tumor cell inoculation was day 0. At days 7, 14 and 21, 0.5×10⁶ FACS-sorted engineered MSCs or the same amount of non-transfected MSCs were administrated by intravenous injection. At days 7, 14, 21 and 28, the mice body weights and tumor growths were monitored by scale or BLI. At day 28, all animals were sacrificed and the whole lung of each mouse was harvested for further ex vivo analysis.

Example 9

BLI

BLI was done using the IVIS200 system (Caliper Life Sciences). Mice were anesthetized with 2% isoflurane in $O_2$ and received intraperitoneal injection of D-luciferin solution in PBS at a dose of 150 mg/kg. Serial images were acquired at 5-20 min after D-luciferin administration (integration, 30 s; binning, 4 s). The BLI signal intensity was quantified as the sum of all detected photon counts within the region of interest after subtraction of background luminescence.

Example 10

H&E Staining

At day 28, the whole lung of each mouse was harvested and fixed in 100 ml of buffered formalin for 24 h. H&E staining was carried out, and the pictures of the stained slides were taken under a light microscope (Zeiss).

Example 11

Statistics

Statistical significance was determined by one-way ANOVA. P values of <0.05 were considered statistically significant.

Example 12

Figure 1B:
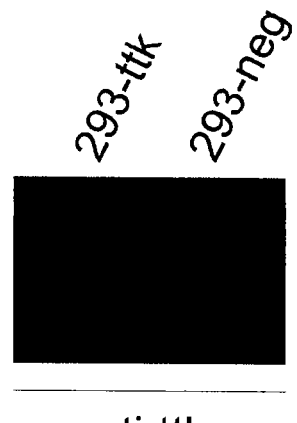
Figure 1C:
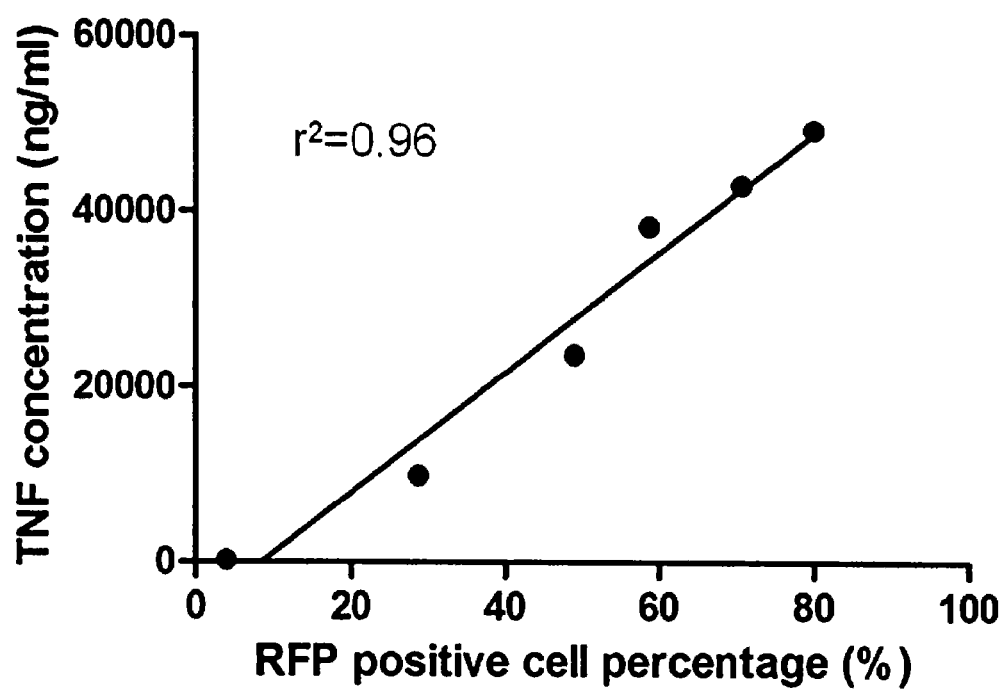

To characterize the dual promoter lentiviral vector pCDH-MSCV-wild-type TNF-RGD4C-EF1-mrfp-ttk, the 293T cells were transduced with the supernatant containing pseudoviral particles. Western blot was conducted to detect expression of TNF and ttk. Secreted TNF-RGD4C fusion protein was successfully detected in the cell culture medium, as shown in FIG. 1A. In addition, the expression of ttk was also observed in transduced 293T cells, as shown in FIG. 1B. To make sure the level of RFP and TNF-RGD4C is comparable, ELISA and FACS assays were performed to verify the correlation between TNF-RGD4C concentrations and RFP expression levels. Correlation between the expression of these two proteins was observed ($r^2$=0.96) as shown in FIG. 1C, which indicated that mrfp-ttk could be used as a gene reporter to sort positive MSCs with expression of therapeutic fusion protein and to track in vivo localization of MSCs.

Example 13

Figure 2A:
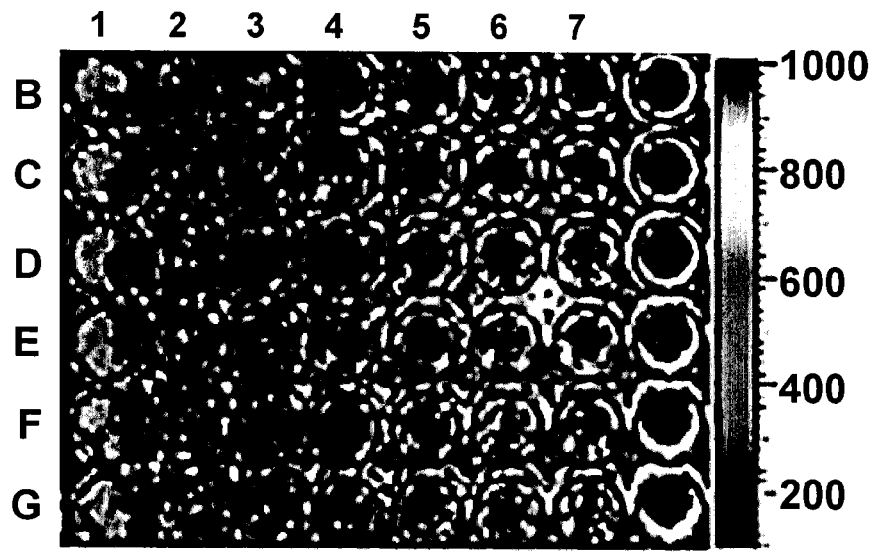
FIG. 2A is a digital image of bioluminescence images of fluc-4T1 after 48 h of incubation with different concentrations of wild-type TNF-RGD4C. Concentrations of columns 1-7 are: 0, 1.1, 2, 2.77, 3.4, 4, and 4.5 pg/ml. The results indicate inhibition of tumor cell proliferation by the secreted wild-type TNF-RGD4C fusion protein.
Figure 2B:
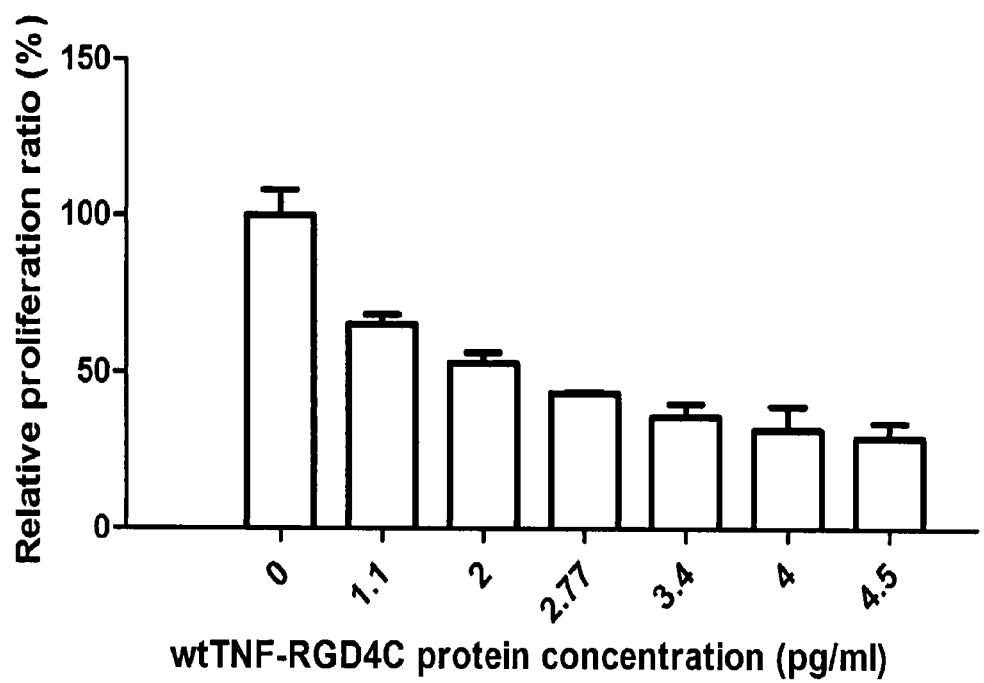
FIG. 2B is a graph illustrating the quantified result of bioluminescence imaging. * P<0.05

To investigate whether the secreted wild-type TNF-RGD4C fusion protein has an inhibitory effect on tumor cell growth, fluc-4T1 cells, a murine breast cancer cell line stably transfected with firefly luciferase, were incubated with different concentrations of wild-type TNF-RGD4C fusion protein that had been obtained from the supernatant of transduced 293 FT cells for 48 h. Cell bioluminescence imaging was then performed to measure and quantify the inhibition effect. It was found that the proliferation of fluc-4T1 was significantly inhibited in the presence of the increasing amount of wild-type TNF-RGD4C and the relative proliferation rate of fLuc-4T1 was reduced up to 33.4%, as shown in FIG. 2.

After verifying that secreted wild-type TNF-RGD4C fusion protein was able to inhibit the tumor cell growth, tumor cells were co-cultured with transduced MSCs to determine whether engineered MSCs could inhibit tumor cell growth by secreting TNF.

Figure 3:
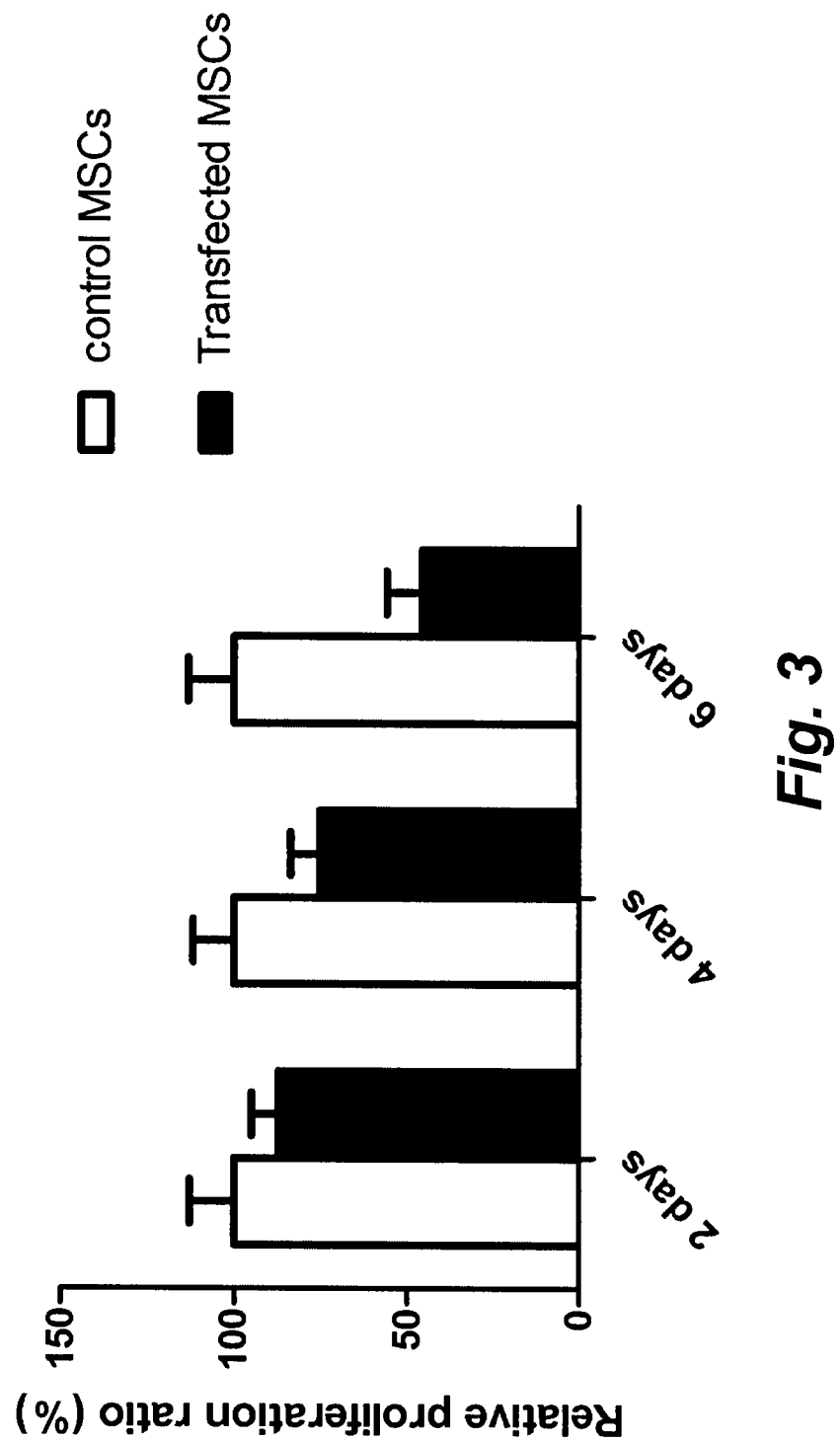
FIG. 3 is a graph illustrating transfected MSCs inhibit tumor cell proliferation by co-culturing with murine breast cancer cell line fLuc-4T1. fLuc-4T1 was co-cultured with the same amount of transfected MSCs or control MSCs in 48-well plates and bioluminescence imaging was conducted at 2, 4 and 6 days of incubation. The relative proliferation ratio was calculated after normalization to the signals from the control group. * P<0.05

The inhibition of tumor proliferation was observed at the second day of co-culturing, and the inhibitory effect was more significant with longer incubation times for 4 or 6 days, as shown in FIG. 3, which indicated the advantages of applying MSCs as delivery vehicles for therapeutic proteins compared to using therapeutic protein alone.

Example 14

Figure 4:
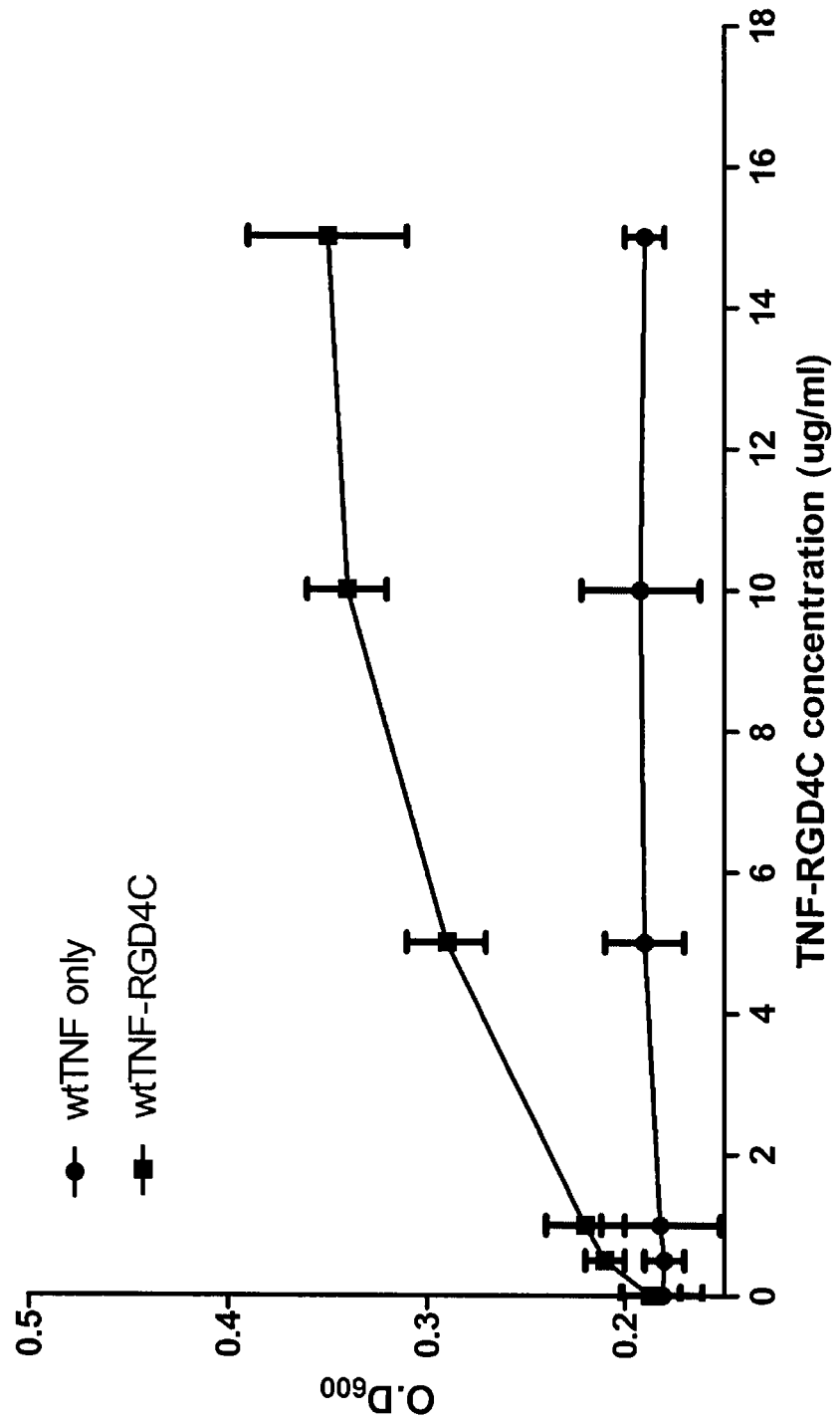
FIG. 4 is a graph illustrating the assessment of the specific binding capability of secreted wild-type TNF-RGD4C.

RGD4C is an integrin $α_vβ_3$ specific ligand and has been recently used for tumor vasculature targeted imaging and therapy (Wu at al., (2008) *Bioconjug Chem.* 19: 1972-1979; Wang et al., (2008) *Mol. Cancer Ther.* 7: 1044-1053). To assess the specific binding function of wild-type TNF-RGD4C, the human glioblastoma cell line U87MG with high expression level of integrin $α_vβ_3$ was used in cell adhesion assay. The $A_{600}$ values from wells with the addition of TNF-RGD4C was significantly higher than that from wells with the addition of only wild-type TNF and the increase of $A_{600}$ paralleled the increase in the concentration of wild-type TNF-RGD4C (FIG. 4), which demonstrated that wild-type TNF-RGD4C has a specific integrin $α_vβ_3$ binding function. This specific binding function is potentially able to assist the binding of the therapeutic fusion protein to tumor blood vessels and integrin $α_vβ_3$-positive tumor cells so as to enhance the in vivo treatment potential.

Example 15

Figure 5A:
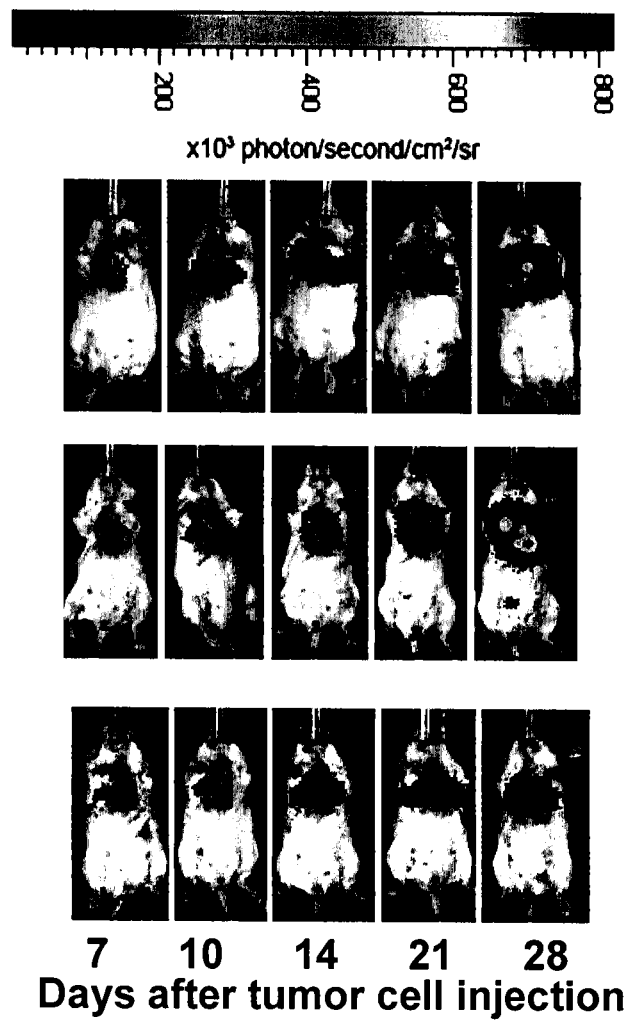
FIG. 5A shows a series of digital images of the results of the in vivo treatment of breast cancer lung metastasis model (n=6 for each group of mice). At day 0, $2 \times 10^4$ of fLuc-4T1 murine breast cancer cells were injected into Balb/c mice intravenously. At days 7, 14, and 21 $0.5 \times 10^6$ transfected MSCs or control MSCs were injected into mice intravenously. Tumor growth was monitored by bioluminescent imaging. Representative bioluminescence images of three groups of mice over the time are shown: (a) no treatment group; (b) group treated with control MSCs; (c) group treated with MSCs expressing wild-type TNF-RGD4C and mrfp-ttk.
Figure 5B:
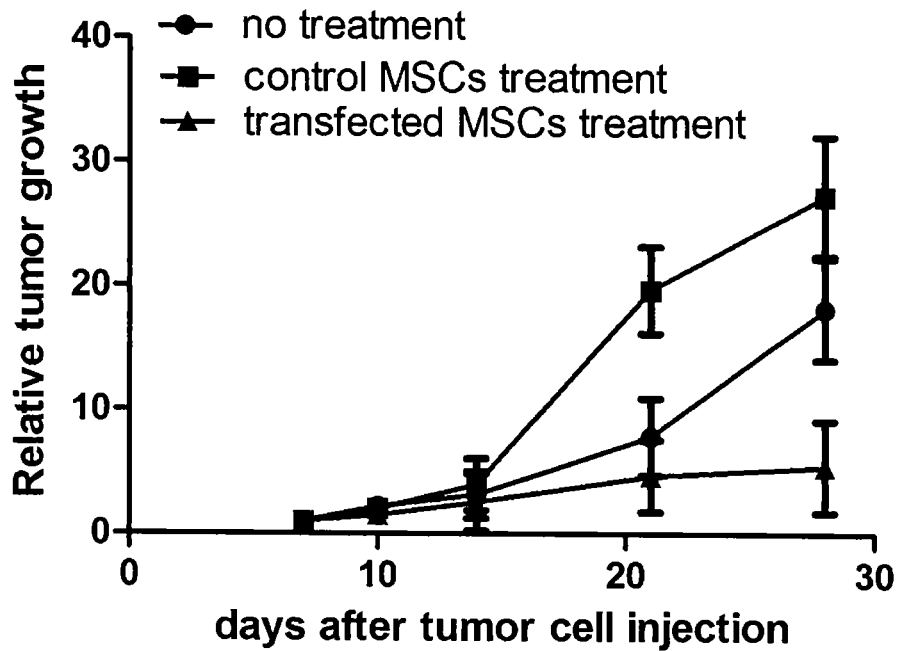
FIG. 5B is a graph illustrating relative tumor growth normalized to the signal from day 7.
Figure 5C:
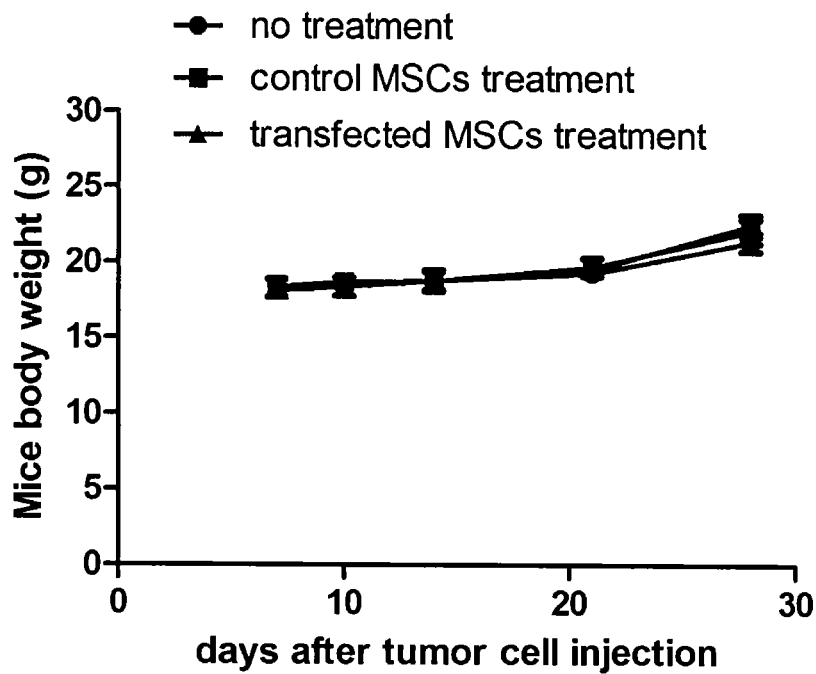
FIG. 5C is a graph illustrating body weight. There was no significant difference on mice body weight between all groups.

In vivo treatments were conducted to evaluate whether the engineered MSCs of the disclosure could be used as a cell-based vehicle to deliver therapeutic proteins to tumor cells. The model used for this purpose was lung metastasis of murine breast cancer. 2×10⁴ of fLuc-4T1 murine breast cancer cells were injected intravenously and bioluminescent imaging was used to monitor tumor growth. From 7 days after tumor cell injection, weekly treatments were started by intravenously injecting $0.5 \times 10^6$ of RFP-sorted transduced MSCs into tumor-bearing mice. Tumor burden and growth were continually monitored by bioluminescence imaging, as shown in FIG. 5A. Mice body weight was measured to monitor side effects of the MSCs injection. Compared to the control MSCs treatment, mice injected with transduced MSCs exhibited much slower tumor growth (P<0.05), as shown in FIG. 5B, without obvious body weight change, as shown in FIG. 5C.

Figure 6A:
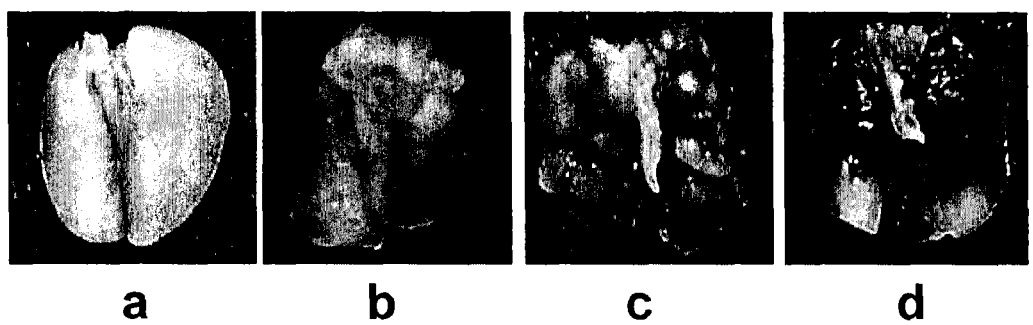
FIGS. 6A and 6B are digital images illustrating representative ex vivo and histology images of grouped lung. Images: a and e, normal lung; b and f, lung of mice injected with fLuc-4T1 only; c and g, lung of mice injected with fLuc-4T1 and control MSCs; d and h, lung of mice injected with transfected MSCs. T: tumor area; N: normal area.
Figure 6B:

Histological analysis was conducted to verify in vivo treatment results. FIG. 6A illustrates representative images of formalin-fixed lung from three groups of mice and normal mice. Compared to normal lung (FIG. 6A, a), tumor nodules were observed from all three groups. Particularly, tumors nodules are widely spread throughout the lung from control MSCs groups, which is consistent with the in vivo imaging result (FIG. 5). There was reduced size and number of tumor nodules in the mouse lung from transfected MSCs treatment groups compared with those from the other two groups. In addition, as shown in FIG. 6A, d, the tissue necrosis areas were caused by the treatment. H&E staining images (FIG. 6B) show the local area of lung with tumor nodules and normal lung tissue. Taken together, ex vivo examination of the lung tissue confirmed the tumor growth inhibition effect of secreted wild-type TNF-RGD4C from transfected MSCs, corroborating the findings based on in vivo imaging.

We claim:

1. A genetically modified mesenchymal stem cell comprising a nucleic acid expression vector comprising an expression cassette, said cassette comprising a nucleic acid sequence operably linked to a gene expression promoter and encoding a heterologous fusion polypeptide, said heterologous polypeptide comprising a tissue necrotic factor region and an integrin-binding region, and wherein the nucleic acid expression vector further comprises a region encoding a reporter polypeptide, wherein the nucleic acid expression vector has the nucleic acid sequence of SEQ ID NO.: 1.

2. A recombinant nucleic acid comprising an expression cassette comprising a nucleic acid sequence operably linked to a gene expression promoter and encoding a heterologous fusion polypeptide, comprising a tissue necrotic factor region and an integrin-binding region and a reporter polypeptide, wherein the recombinant nucleic acid is inserted in a lentivirus-based nucleic acid expression vector, wherein said recombinant nucleic acid has the nucleic acid sequence of SEQ ID NO.: 1.

3. The recombinant nucleic acid of claim 2, wherein the integrin-binding region comprises the motif arginine-glycine-aspartate.

4. The recombinant nucleic acid of claim 2, wherein the expressed integrin-binding region has the amino acid sequence of SEQ ID NO: 8.

* * * * *